(12) United States Patent
Elokdah et al.

(10) Patent No.: US 7,790,751 B2
(45) Date of Patent: Sep. 7, 2010

(54) AZINYL-3-SULFONYLINDAZOLE DERIVATIVES AS 5-HYDROXYTRYPTAMINE-6 LIGANDS

(75) Inventors: Hassan Mahmoud Elokdah, North Wales, PA (US); Alexander Alexei Greenfield, West Windsor, NJ (US); Kevin Liu, West Windsor, NJ (US); Geraldine Ruth McFarlane, Monmouth Junction, NJ (US); Cristina Grosanu, Keansburg, NJ (US); Jennifer Rebecca Lo, Plainsboro, NJ (US); Albert Jean Robichaud, Ringoes, NJ (US)

(73) Assignee: Wyeth LLC, New York, NY (US)

( * ) Notice: Subject to any disclaimer, the term of this patent is extended or adjusted under 35 U.S.C. 154(b) by 1037 days.

(21) Appl. No.: 11/504,243

(22) Filed: Aug. 14, 2006

(65) Prior Publication Data
US 2007/0054896 A1    Mar. 8, 2007

Related U.S. Application Data

(60) Provisional application No. 60/708,317, filed on Aug. 15, 2005.

(51) Int. Cl.
*A61K 31/454* (2006.01)
*C07D 403/02* (2006.01)

(52) U.S. Cl. ............ 514/322; 514/323; 546/199; 546/201

(58) Field of Classification Search ............... 514/322, 514/323; 546/199, 201
See application file for complete search history.

(56) References Cited

U.S. PATENT DOCUMENTS

| | | | |
|---|---|---|---|
| 6,391,872 B1 | 5/2002 | Marfat | |
| 6,716,837 B1 | 4/2004 | Edwards et al. | |
| 6,727,246 B2 | 4/2004 | Bernotas et al. | |
| 6,767,912 B2 * | 7/2004 | Zhou et al. | 514/300 |
| 6,815,456 B2 | 11/2004 | Zhou et al. | |
| 6,831,094 B2 * | 12/2004 | Li et al. | 514/414 |
| 6,995,176 B2 | 2/2006 | Bernotas et al. | |
| 2004/0024210 A1 | 2/2004 | Johansson et al. | |
| 2004/0138286 A1 | 7/2004 | Imazaki et al. | |
| 2004/0167122 A1 | 8/2004 | Bernotas et al. | |
| 2005/0113283 A1 | 5/2005 | Solow-Cordero et al. | |
| 2005/0215595 A1 | 9/2005 | Arora et al. | |

OTHER PUBLICATIONS

Kevin W. Hunt et al., "Selective Synthesis of 1-Functionalized-alkyl-1H-indazoles", Organic Letters, 2009, 11 (21), 5054-5057.
William D. Kingsbury et al, "Synthesis of 1- and 2-substituted indazoles as anthelmintic agents", Journal of Medicinal Chemistry, 1976, 19 (6), 839-840.

* cited by examiner

*Primary Examiner*—Celia Chang
(74) *Attorney, Agent, or Firm*—Jennifer A. Kispert; Garth C. Butterfield

(57) ABSTRACT

The present invention provides a compound of formula I and the use thereof for the treatment of a central nervous system disorder related to or affected by the 5-HT6 receptor.

(I)

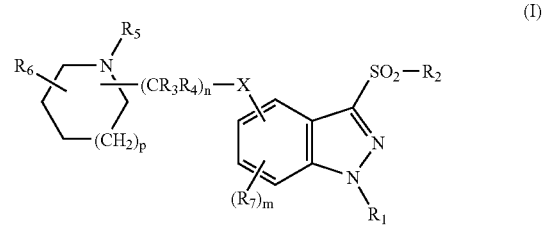

14 Claims, No Drawings

AZINYL-3-SULFONYLINDAZOLE DERIVATIVES AS 5-HYDROXYTRYPTAMINE-6 LIGANDS

This application claims the benefit under 35 U.S.C. §119 (e) to co-pending U.S. provisional application No. 60/708,317, filed Aug. 15, 2005, which is hereby incorporated by reference in its entirety.

BACKGROUND OF THE INVENTION

Serotonin (5-hydroxytryptamine) (5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320-327) and subsequently from human tissue (Kohen, R.; Metcalf, M. A.; Khan, N.; Druck, T.; Huebner, K.; Sibley, D. R. *Journal of Neurochemistry* 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268-276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105-1111).

There are many potential therapeutic uses for 5-HT6 ligands in humans based on direct effects and on indications from available scientific studies. These studies provided information including the localization of the receptor, the affinity of ligands with known in vivo activity, and results obtained from various animal studies conducted so far (Woolley, M. L.; Marsden, C. A.; Fone, K. C. F. *Current Drug Targets: CNS & Neurological Disorders* 2004, 3(1), 59-79).

One therapeutic use of modulators of 5-HT6 receptor function is in the enhancement of cognition and memory in human diseases such as Alzheimer's. The high levels of receptor found in important structures in the forebrain, including the caudate/putamen, hippocampus, nucleus accumbens, and cortex indicate a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; El Mestikawy, S. *Brain Research*, 1997, 746, 207-219). The ability of known 5-$HT_6$ receptor ligands to enhance cholinergic transmission also supported the cognition use (Bentley, J. C.; Boursson, A.; Boess, F. G.; Kone, F. C.; Marsden, C. A.; Petit, N.; Sleight, A. J. *British Journal of Pharmacology*, 1999, 126(7), 1537-1542). Studies have demonstrated that a known 5-$HT_6$ selective antagonist significantly increased glutamate and aspartate levels in the frontal cortex without elevating levels of noradrenaline, dopamine, or 5-HT. This selective elevation of neurochemicals known to be involved in memory and cognition indicates the role 5-$HT_6$ ligands play in cognition (Dawson, L. A.; Nguyen, H. Q.; Li, P. *British Journal of Pharmacology*, 2000, 130(1), 23-26). Animal studies of memory and learning with a known selective 5-$HT_6$ antagonist found positive effects (Rogers, D. C.; Hatcher, P. D.; Hagan, J. J. *Society of Neuroscience, Abstracts* 2000, 26, 680). More recent studies have supported this finding in several additional animal models of cognition and memory including in a novel object discrimination model (King, M. V.; Sleight, A. J.; Wooley, M. L.; Topham, I. A.; Marsden, C. A.; Fone, K. C. F. *Neuropharmacology* 2004, 47(2), 195-204 and Wooley, M. L.; Marsden, C. A.; Sleight, A. J.; Fone, K. C. F. *Psychopharmacology*, 2003, 170(4), 358-367) and in a water maze model (Rogers, D. C.; Hagan, J. J. *Psychopharmacology*, 2001, 158(2), 114-119 and Foley, A. G.; Murphy, K. J.; Hirst, W. D.; Gallagher, H. C.; Hagan, J. J.; Upton, N.; Walsh, F. S.; Regan, C. M. *Neuropsychopharmacology* 2004, 29(1), 93-100).

A related therapeutic use for 5-$HT_6$ ligands is the treatment of attention deficit disorders (ADD, also known as Attention Deficit Hyperactivity Disorder or ADHD) in both children and adults. Because 5-$HT_6$ antagonists enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901-5907), 5-$HT_6$ antagonists attenuate attention deficit disorders.

Early studies examining the affinity of various CNS ligands with known therapeutic utility or a strong structural resemblance to known drugs implicates 5-$HT_6$ ligands in the treatment of schizophrenia and depression. For example, clozapine (an effective clinical antipsychotic) has high affinity for the 5-$HT_6$ receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319-334).

Further, recent in vivo studies in rats indicate that 5-$HT_6$ modulators are useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606-1612).

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

SUMMARY OF THE INVENTION

The present invention provides a 3-sulfonylindazole compound of formula I

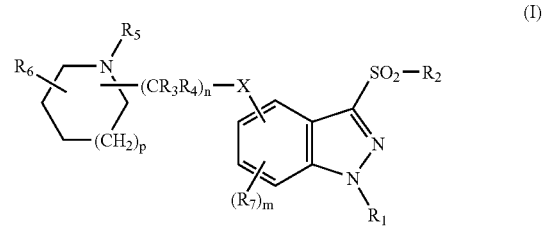

wherein
X is O, S, NR, $CH_2$, CO, $CH_2O$, $CH_2S$, $CH_2NR$, $CH_2CO$, CONR or NRCO;

n is 0 or an integer of 1, 2, 3, 4, 5, or 6;

R is H or an optionally substituted alkyl group;

$R_1$ is H or an alkyl, cycloalkyl, aryl or heteroaryl group each optionally substituted;

$R_2$ is an optionally substituted alkyl, cycloalkyl, aryl or heteroaryl group or an optionally substituted 8- to 13-membered bicyclic or tricyclic ring system having a N atom at the bridgehead and optionally containing 1, 2 or 3 additional heteroatoms selected from N, O or S;

$R_3$ and $R_4$ are each independently H, or an optionally substituted alkyl group;

$R_5$ is H, $COR_{12}$ or an alkyl, alkenyl, alkynyl, cycloalkyl, cycloheteroalkyl, aryl or heteroaryl group each optionally substituted;

$R_6$ is H or an optionally substituted alkyl group;

p is 0 or an integer of 1 or 2;

$R_7$ is H, halogen, CN, $OR_8$, $CO_2R_9$, $CONR_{10}R_{11}$, or an alkyl, alkenyl, alkynyl, cycloalkyl, cycloheteroalkyl, aryl or heteroaryl group each optionally substituted;

m is an integer of 1, 2 or 3;

$R_8$ is H, $COR_{12}$ or an alkyl, alkenyl, alkynyl, aryl or heteroaryl group each optionally substituted;

$R_9$ is H or a $C_1$-$C_6$alkyl, aryl or heteroaryl group each optionally substituted;

$R_{10}$ and $R_{11}$ are each independently H or an optionally substituted alkyl group; and $R_{12}$ is an optionally substituted $C_1$-$C_6$alkyl, cycloalkyl, cycloheteroalkyl, aryl or heteroaryl group; or a stereoisomer thereof or a pharmaceutically acceptable salt thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor has been identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104-109, Pharma Press Ltd and Woolley, M. L.; Marsden, C. A.; Fone, K. C. F. *Current Drug Targets: CNS & Neurological Disorders* 2004, 3(1), 59-79.

Surprisingly, it has now been found that 3-sulfonylindazole compounds of formula I demonstrate 5-HT6 receptor affinity along with significant receptor sub-type selectivity. Advantageously, said formula I compounds are effective therapeutic agents for the treatment of central nervous system (CNS) disorders associated with or affected by the 5-HT6 receptor. Accordingly, the present invention provides a 3-sulfonylindazole compound of formula I

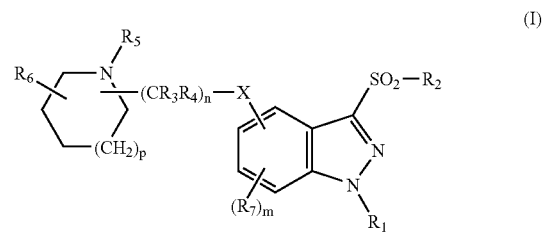

wherein
X is O, S, NR, $CH_2$, CO, $CH_2O$, $CH_2S$, $CH_2NR$, $CH_2CO$, CONR or NRCO;

n is 0 or an integer of 1, 2, 3, 4, 5, or 6;

R is H or an optionally substituted alkyl group;

$R_1$ is H or an alkyl, cycloalkyl, aryl or heteroaryl group each optionally substituted;

$R_2$ is an optionally substituted alkyl, cycloalkyl, aryl or heteroaryl group or an optionally substituted 8- to 13-membered bicyclic or tricyclic ring system having a N atom at the bridgehead and optionally containing 1, 2 or 3 additional heteroatoms selected from N, O or S;

$R_3$ and $R_4$ are each independently H, or an optionally substituted alkyl group;

$R_5$ is H, $COR_{12}$ or an alkyl, alkenyl, alkynyl, cycloalkyl, cycloheteroalkyl, aryl or heteroaryl group each optionally substituted;

$R_6$ is H or an optionally substituted alkyl group;

p is 0 or an integer of 1 or 2;

$R_7$ is H, halogen, CN, $OR_8$, $CO_2R_9$, $CONR_{10}R_{11}$, or an alkyl, alkenyl, alkynyl, cycloalkyl, cycloheteroalkyl, aryl or heteroaryl group each optionally substituted;

m is an integer of 1, 2 or 3;

$R_8$ is H, $COR_{12}$ or an alkyl, alkenyl, alkynyl, aryl or heteroaryl group each optionally substituted;

$R_9$ is H or a $C_1$-$C_6$alkyl, aryl or heteroaryl group each optionally substituted;

$R_{10}$ and $R_{11}$ are each independently H or an optionally substituted alkyl group; and $R_{12}$ is an optionally substituted $C_1$-$C_6$alkyl, cycloalkyl, cycloheteroalkyl, aryl or heteroaryl group; or a stereoisomer thereof or a pharmaceutically acceptable salt thereof.

It is understood that the claims encompass all possible stereoisomers and prodrugs. Moreover, unless stated otherwise, each alkyl, alkenyl, alkynyl, cycloalkyl cycloheteroalkyl, aryl or heteroaryl group is contemplated as being optionally substituted.

An optionally substituted moiety may be substituted with one or more substituents. The substituent groups, which are optionally present, may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term "alkyl" includes both straight chain and branched-chain (unless defined otherwise) monovalent saturated hydrocarbon moiety of 1-12 carbon atoms, preferably 1-6 carbon atoms, more preferably 'lower' alkyl of 1-4 carbon atoms. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Alkyl groups can be optionally substituted. Suitable alkyl substitutions include, but are not limited to, CN, OH, halogen, phenyl, carbamoyl, carbonyl, alkoxy or aryloxy.

As used herein the term "haloalkyl" designates a $C_nH_{2n+1}$ group having from one to 2n+1 halogen atoms which may be the same or different. Examples of haloalkyl groups include $CF_3$, $CH_2Cl$, $C_2H_3BrCl$, $C_3H_5F_2$, or the like.

The term "halogen", as used herein, designates fluorine, chlorine, bromine, and iodine.

The term "alkenyl", as used herein, refers to either a straight chain or branched-chain monovalent hydrocarbon moiety containing at least one double bond bond and having from 2-12 carbon atoms, preferably 2-6 carbon atoms, more preferably 2-4 carbon atoms. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like.

The term "alkynyl", as used herein, refers to an alkyl group having one or more triple carbon-carbon bonds. Alkynyl groups preferably contain 2 to 6 carbon atoms. Examples of alkynyl groups include, but are not limited to, ethynyl, propynyl, butynyl, pentynyl, and the like. In some embodiments, alkynyl groups can be substituted with up to four substituent groups, as described below.

The term "cycloalkyl", as used herein, refers to a monocyclic, bicyclic, tricyclic, fused, bridged, or spiro monovalent saturated carbocyclic moiety of 3-10 carbon atoms, unless otherwise specified. Any suitable ring position of the cycloalkyl moiety may be covalently linked to the defined chemical structure. Examples of cycloalkyl moieties include, but are not limited to, chemical groups such as cyclopropyl, cyclobutyl, cyclopentyl, cyclohexyl, cycloheptyl, norbornyl, adamantyl, spiro[4.5]decanyl, and homologs, isomers, or the like.

The term "cycloheteroalkyl" as used herein designates a non-aromatic 3-10 membered e.g. a 5-7 membered ring system containing 1, 2 or 3 heteroatoms, which may be the same or different, selected from N, O or S and optionally containing one double bond. Exemplary of the cycloheteroalkyl ring systems included in the term as designated herein are the following rings wherein $X_1$ is NR', O or S and R is H or an optional substituent as defined hereinbelow.

 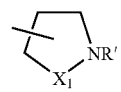  

-continued

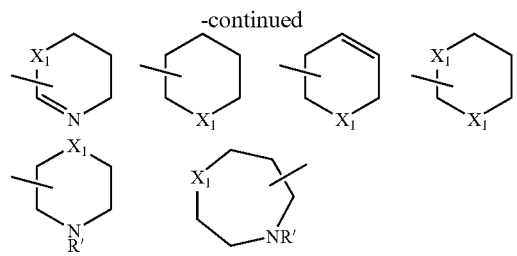

The term "aryl", as used herein, refers to an aromatic carbocyclic moiety of up to 20 carbon atoms, e.g. 6-20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, biphenyl, anthryl, phenanthryl, fluorenyl, indanyl, biphenylenyl, acenaphthenyl, acenaphthylenyl, and the like.

The term "heteroaryl" as used herein designates an aromatic heterocyclic ring system, e.g. having from 5-20 ring atoms, which may be a single ring (monocyclic) or multiple rings (bicyclic, up to three rings) fused together or linked covalently. Preferably, heteroaryl is a 5- to 6-membered ring. The rings may contain from one to four hetero atoms selected from nitrogen, oxygen, or sulfur, wherein the nitrogen or sulfur atom(s) are optionally oxidized, or the nitrogen atom(s) are optionally quarternized. Any suitable ring position of the heteroaryl moiety may be covalently linked to the defined chemical structure. Examples of heteroaryl moieties include, but are not limited to, heterocycles such as furan, thiophene, pyrrole, pyrazole, imidazole, oxazole, isoxazole, thiazole, isothiazole, oxadiazole, triazole, pyridine, pyrimidine, pyrazine, pyridazine, benzimidazole, benzoxazole, benzisoxazole, benzothiazole, benzofuran, benzothiophene, thianthrene, dibenzofuran, dibenzothiophene, indole, indazole, quinoline, isoquinoline, quinazoline, quinoxaline, purine, or the like.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein W is NR', O or S; and R' is H or an optional substituent as described hereinbelow:

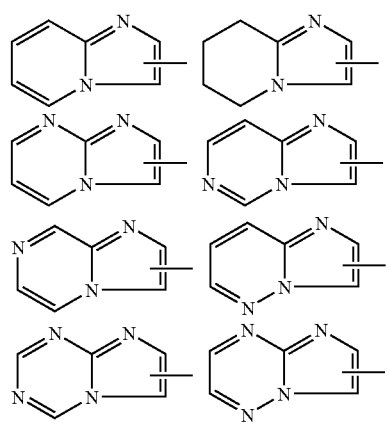

-continued

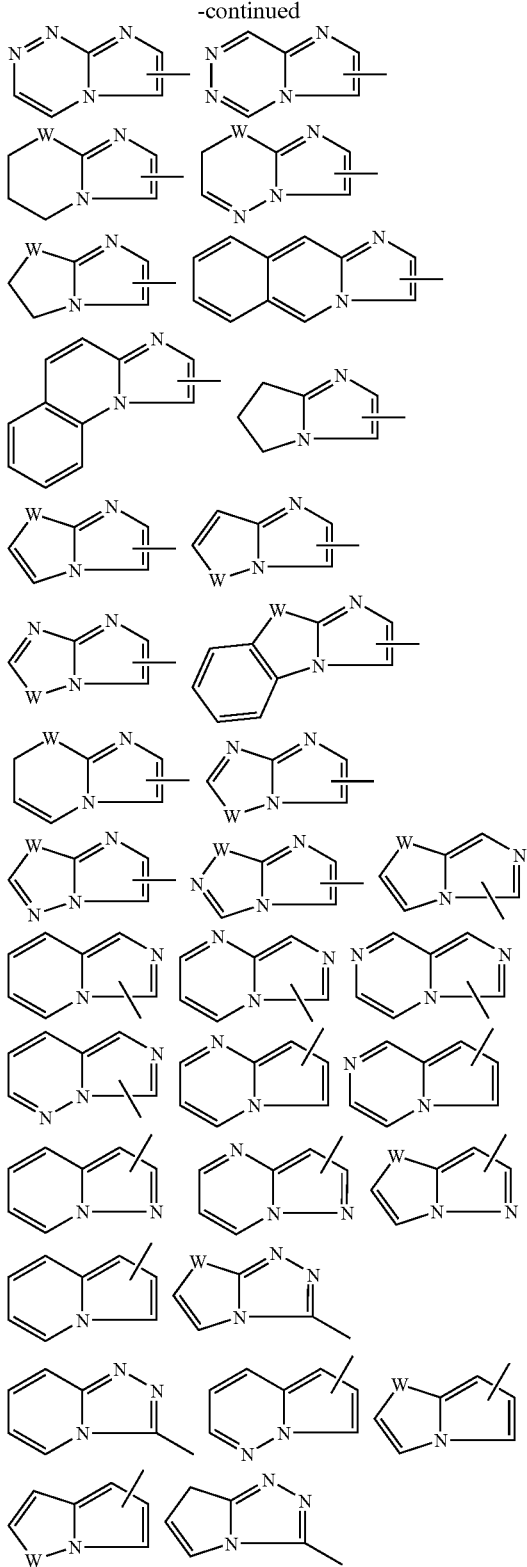

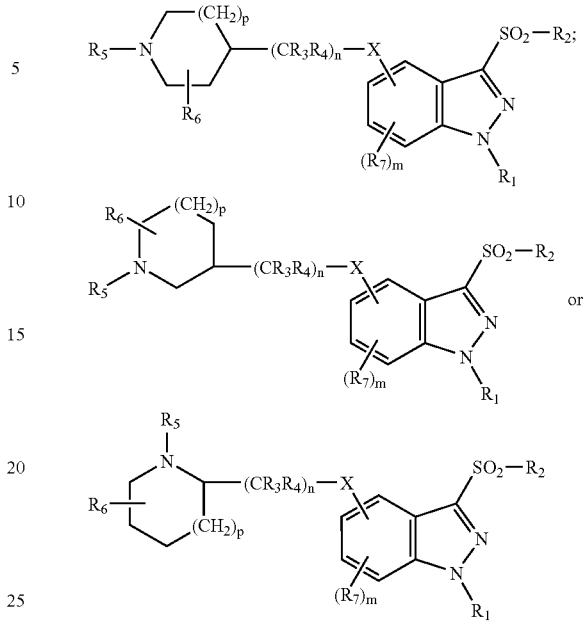

The compounds of this invention are limited to those that are chemically feasible and stable. Therefore, a combination of substituents or variables in the compounds described above is permissible only if such a combination results in a stable or chemically feasible compound.

While shown without respect to stereochemistry, compounds of formula I include all stereochemical forms of the structure; i.e., the R and S configurations for each asymmetric center. Therefore, single stereochemical isomers as well as enantiomeric and diastereomeric mixtures of the present compounds are within the scope of the invention. The compounds of this invention may contain one or more asymmetric centers and may thus give rise to optical isomers and diastereomers. the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one stereoisomer, preferably less than about 50%, more preferably less than about 75%, and even more preferably less than about 90%.

Formula I structures depicted herein are also meant to include compounds which differ only in the presence of one or more isotopically enriched atoms. For example, compounds having the present structure except for the replacement of a hydrogen by a deuterium or tritium, or the replacement of a carbon by a $^{13}C$- or $^{14}C$-enriched carbon are within the scope of this invention.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as For the formula I compounds of the invention, it is intended the azine ring be attached to the $(CR_3R_4)_n$ group through a ring carbon atom or, in the instance where n is zero, the azine ring is attached directly to the X group through a ring carbon atom. For example:

morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived from organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Preferred compounds of the invention are those compounds of formula I wherein X is O, NR or $CH_2$. Another group of preferred compounds is those formula I compounds wherein n is 0 or 1. Also preferred are those formula I compounds wherein $R_2$ is an optionally substituted aryl or heteroaryl group or an optionally substituted 8- to 13-membered bicyclic or tricyclic ring system having a N atom at the bridgehead and optionally containing 1, 2 or 3 additional heteroatoms selected from N, O or S.

More preferred compounds of the invention are those compounds of formula I wherein X is O and $R_5$ is H or $C_1$-$C_4$ alkyl. Another group of more preferred compounds is those compounds of formula I wherein X is O and n is 0. A further group of more preferred compounds are those compounds of formula I wherein X is O; n is 0 and p is 0 or 1.

Among the preferred compounds of the invention are:
5-[(1-butylpyrrolidin-3-yl)oxy]-3-(1-naphthylsulfonyl)-1H-indazole;
3-(1-naphthylsulfonyl)-5-[(1-propylpyrrolidin-3-yl)oxy]-1H-indazole;
5-[(1-isopropylpyrrolidin-3-yl)oxy]-3-(1-naphthylsulfonyl)-1H-indazole;
5-[(1-methylpyrrolidin-3-yl)oxy]-3-(1-naphthylsulfonyl)-1H-indazole;
3-(1-naphthylsulfonyl)-5-(piperidin-4-yloxy)-1H-indazole;
3-(1-naphthylsulfonyl)-5-[(1-propylpiperidin-4-yl)oxy]-1H-indazole;
5-[(1-butylpiperidin-4-yl)oxy]-3-(1-naphthylsulfonyl)-1H-indazole;
5-[(1-methylpiperidin-4-yl)oxy]-3-(1-naphthylsulfonyl)-1H-indazole;
5-[(1-isopropylpiperidin-4-yl)oxy]-3-(1-naphthylsulfonyl)-1H-indazole;
3-(1-naphthylsulfonyl)-5-{[1-(2-phenylethyl)piperidin-4-yl]oxy}-1H-indazole;
5-[(1-ethylpiperidin-4-yl)oxy]-3-(1-naphthylsulfonyl)-1H-indazole;
5-[(1-ethylpyrrolidin-3-yl)oxy]-3-(1-naphthylsulfonyl)-1H-indazole;
3-(1-naphthylsulfonyl)-5-{[1-(2-phenylethyl)pyrrolidin-3-yl]oxy}-1H-indazole;
3-(1-naphthylsulfonyl)-5-(piperidin-4-ylmethoxy)-1H-indazole;
3-(1-naphthylsulfonyl)-5-(piperidin-3-ylmethoxy)-1H-indazole;
3-(1-naphthylsulfonyl)-5-(piperidin-3-yloxy)-1H-indazole;
3-(1-naphthylsulfonyl)-N-piperidin-4-yl-1H-indazol-5-amine;
3-(1-naphthylsulfonyl)-N-(piperidin-4-ylmethyl)-1H-indazol-5-amine;
3-(1-naphthylsulfonyl)-N-piperidin-3-yl-1H-indazol-5-amine;
N-[3-(1-naphthylsulfonyl)-1H-indazol-5-yl]piperidine-4-carboxamide;
3-(1-naphthylsulfonyl)-N-piperidin-4-yl-1H-indazol-6-amine;
3-(1-naphthylsulfonyl)-N-piperidin-3-yl-1H-indazol-6-amine;
3-(1-naphthylsulfonyl)-N-(piperidin-4-ylmethyl)-1H-indazol-6-amine;
N-[3-(1-naphthylsulfonyl)-1H-indazol-6-yl]piperidine-4-carboxamide;
3-(1-naphthylsulfonyl)-N-piperidin-4-yl-1H-indazol-7-amine;
3-(1-naphthylsulfonyl)-N-piperidin-3-yl-1H-indazol-7-amine;
3-(1-naphthylsulfonyl)-N-(piperidin-4-ylmethyl)-1H-indazol-7-amine;
N-[3-(1-naphthylsulfonyl)-1H-indazol-7-yl]piperidine-4-carboxamide;
N-[3-(1-naphthylsulfonyl)-1H-indazol-7-yl]piperidine-3-carboxamide;
3-(1-naphthylsulfonyl)-N-piperidin-4-yl-1H-indazol-4-amine;
3-(1-naphthylsulfonyl)-N-piperidin-3-yl-1H-indazol-4-amine;
3-(1-naphthylsulfonyl)-N-(piperidin-4-ylmethyl)-1H-indazol-4-amine;
3-(phenylsulfonyl)-5-(piperidin-4-yloxy)-1H-indazole;
3-[(3-fluorophenyl)sulfonyl]-5-(piperidin-4-yloxy)-1H-indazole;
3-[(2-chlorophenyl)sulfonyl]-5-(piperidin-4-yloxy)-1H-indazole;
3-[(3-chlorophenyl)sulfonyl]-5-(piperidin-4-yloxy)-1H-indazole;
3-[(4-chlorophenyl)sulfonyl]-5-(piperidin-4-yloxy)-1H-indazole;
3-[(3-methylphenyl)sulfonyl]-5-(piperidin-4-yloxy)-1H-indazole;
3-[(3-methoxyphenyl)sulfonyl]-5-(piperidin-4-yloxy)-1H-indazole;
3-[(4-methoxyphenyl)sulfonyl]-5-(piperidin-4-yloxy)-1H-indazole;
5-(piperidin-4-yloxy)-3-{[3-(trifluoromethyl)phenyl]sulfonyl}-1H-indazole;
5-(piperidin-4-yloxy)-3-{[4-(trifluoromethyl)phenyl]sulfonyl}-1H-indazole;
3-[(4-isopropylphenyl)sulfonyl]-5-(piperidin-4-yloxy)-1H-indazole;
3-[(4-methyl-1-naphthyl)sulfonyl]-5-(piperidin-4-yloxy)-1H-indazole;
3-[(3-chlorophenyl)sulfonyl]-N-piperidin-4-yl-1H-indazol-5-amine;

3-[(4-chlorophenyl)sulfonyl]-N-piperidin-4-yl-1H-indazol-5-amine;
3-(2-naphthylsulfonyl)-N-piperidin-4-yl-1H-indazol-5-amine;
3-[(3-fluorophenyl)sulfonyl]-N-piperidin-4-yl-1H-indazol-5-amine;
3-[(4-fluorophenyl)sulfonyl]-N-piperidin-4-yl-1H-indazol-5-amine;
3-[(4-isopropylphenyl)sulfonyl]-N-piperidin-4-yl-1H-indazol-5-amine;
N-piperidin-4-yl-3-{[4-(trifluoromethyl)phenyl]sulfonyl}-1H-indazol-5-amine;
3-(phenylsulfonyl)-N-piperidin-4-yl-1H-indazol-5-amine;
3-[(4-methoxyphenyl)sulfonyl]-N-piperidin-4-yl-1H-indazol-5-amine;
3-[(3-methylphenyl)sulfonyl]-N-piperidin-4-yl-1H-indazol-5-amine;

a stereoisomer thereof; or a pharmaceutically acceptable salt thereof.

Advantageously, the present invention also provides a convenient and effective process for the preparation of a compound of formula I which comprises reacting a compound of formula II with $NaNO_2$ in the presence an acid optionally in the presence of a solvent to give the compound of formula I wherein $R_1$ is H; and optionally reacting said compound with $R_1$-Hal wherein Hal is Cl, Br or I and $R_1$ is an alkyl, cycloalkyl aryl or heteroaryl group each optionally substituted. The process is shown hereinbelow in flow diagram I.

FLOW DIAGRAM I

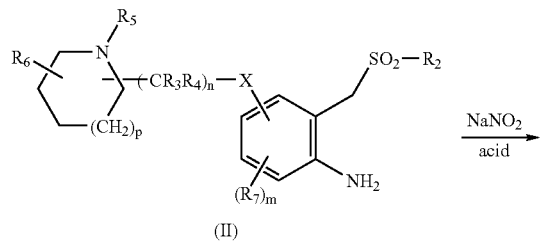

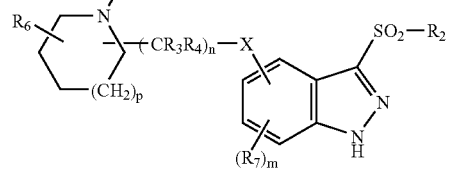

Acids suitable for use in the process of the invention include acids such as HCl, HBR, $H_2SO4$, $H_3PO_4$ or any conventional mineral acid, preferably HCl.

Solvents suitable for use in the process of the invention include alkanols such as methanol, ethanol, isopropanol, butanol, or the like; water or a mixture thereof.

Compounds of formula II may be prepared using conventional synthetic methods and, if required, standard isolation or separation techniques. For example, compounds of formula II wherein X is O and $R_5$ is other than H (IIa) may be prepared by the reaction of an amino alcohol 1 with either a fluoro-nitrobenzene 2 under basic conditions, or a nitrophenol 3 under Mitsunobu conditions, to give the compound 4. Compound 4 is reacted with a chlorosulfone 5, followed by hydrogenation, to give the desired compound of formula IIa. The reaction is shown in flow diagram II.

FLOW DIAGRAM II

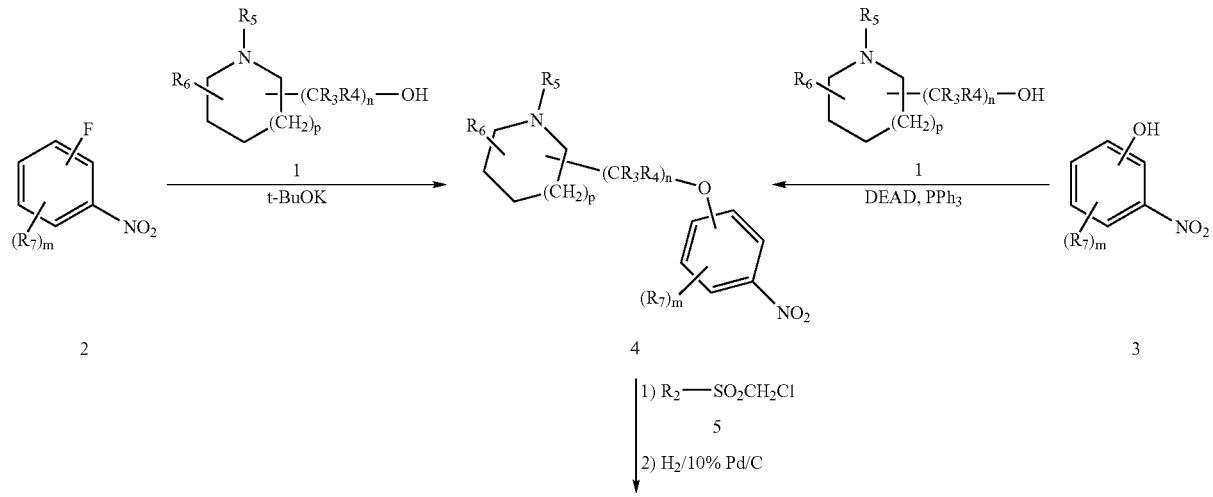

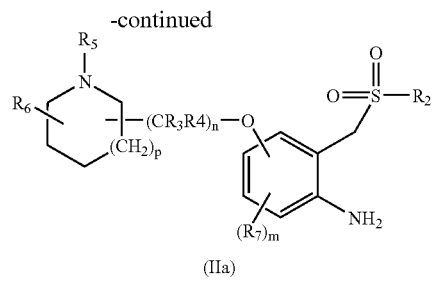

(IIa)

Compounds of formula IIa may then be converted to compounds of formula I wherein X is O and $R_5$ is other than H as shown hereinabove in flow diagram I.

Compounds of formula I wherein X is O and $R_5$ is H (Ia) may be obtained by reacting a compound of formula II wherein $R_5$ is a protecting group (IIb) with $NaNO_2$ and aqueous HCl to give the protected formula I compound (IP) and deprotecting IP to give the desired compound of formula Ia wherein $R_1$ is H or reacting IP with the halide, $R_1$-Hal, followed by deprotection, to give the desired compound of formula Ia wherein $R_1$ is other than H. The reactions are shown in flow diagram III wherein P is a protecting group and Hal is Cl, Br or I.

Suitable protecting groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethyl- carbonyl (Fmoc), formyl, acetyl, chloroacetyl, dichloroacetyl, trichloroacetyl, phenylacetyl, trifluoroacetyl, benzoyl, or any protecting group known to be suitable to protect an amine in organic synthetic procedures.

Compounds of formula I wherein X is NR and R and $R_1$ are H (Ib) or X is NRCO and R and $R_1$ are H (Ic) may be prepared by reacting a nitroindazole 7 with iodine to give the corresponding 3-iodoindazole 8; coupling 8 with a thiol 9, followed by oxidation with a suitable oxidizing agent such as m-chloroperbenzoic acid (mCPBA), to give the sulfone 10; reducing the nitro group of 10 with Sn/HCl or $SnCl_2$/HCl to obtain the corresponding amine 11; and either reacting 11 with the aldehyde 12 under reductive amination conditions to afford the desired compound of formula Ib, or coupling 11 with an acid 13 to give the desired compound of formula Ic. The reactions are shown in flow diagram IV hereinbelow, wherein Ac represents $COCH_3$.

FLOW DIAGRAM III

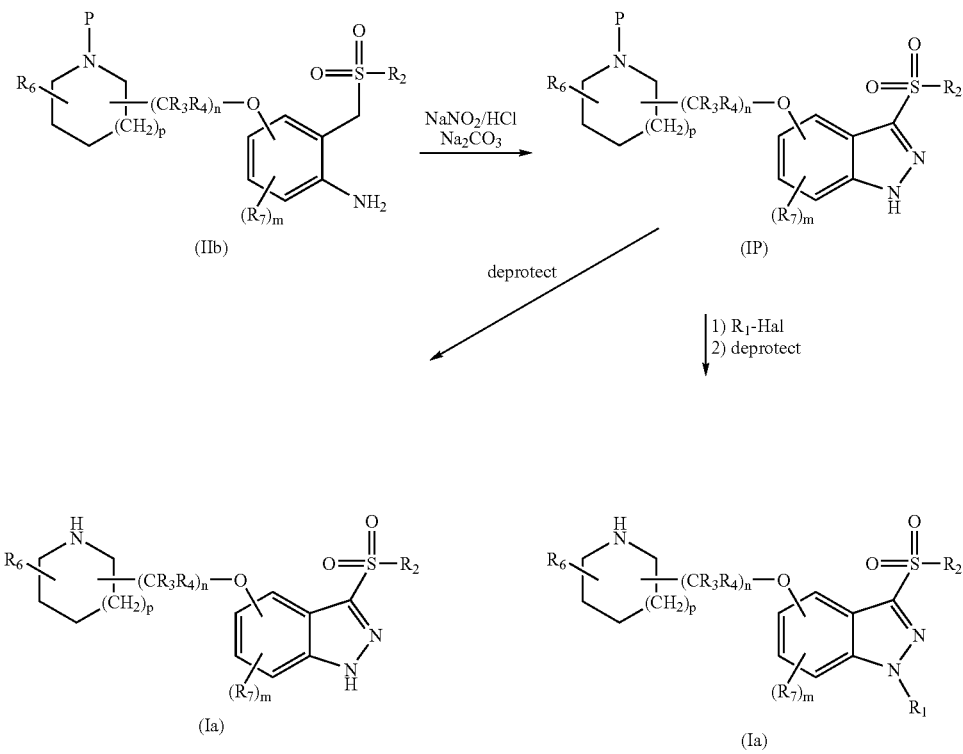

FLOW DIAGRAM IV

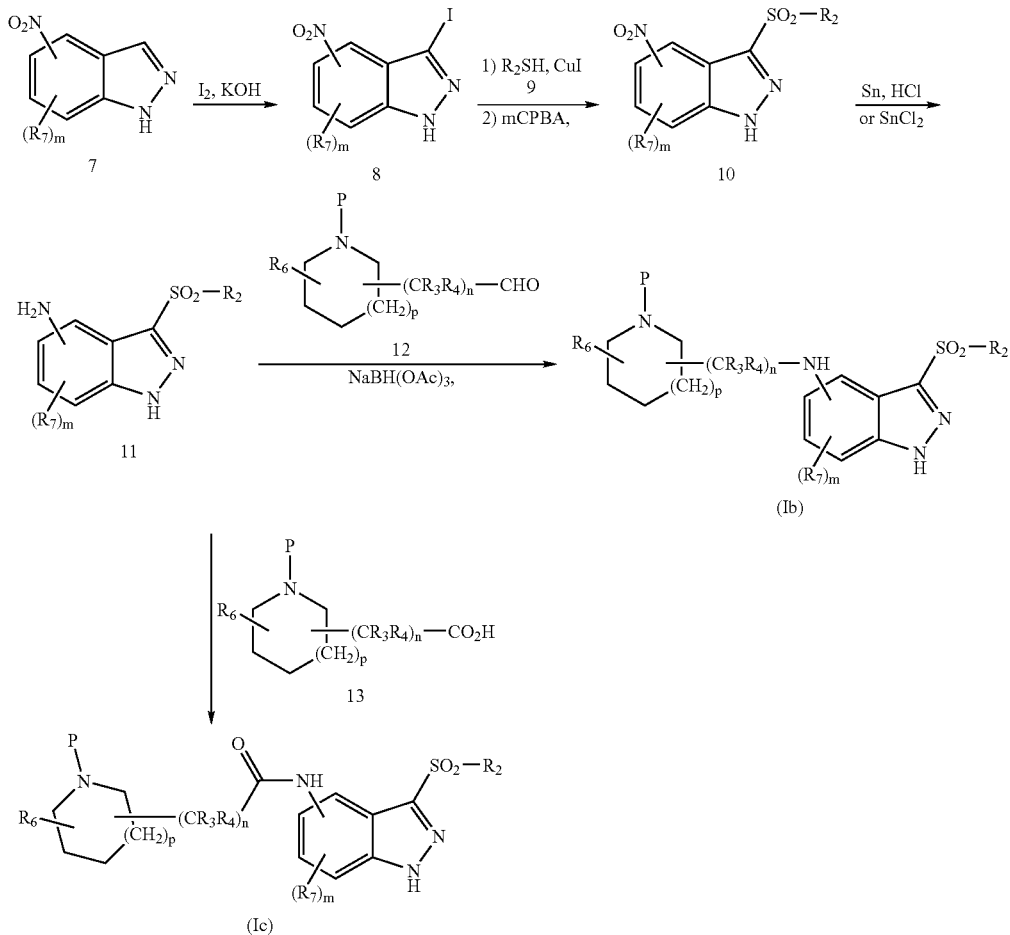

Advantageously, the formula I compounds of the invention are useful for the treatment of CNS disorders related to or affected by the 5-HT6 receptor including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The inventive method includes: a method for the treatment of schizophrenia; a method for the treatment of a disease associated with a deficit in memory, cognition, and/or learning or a cognitive disorder such as Alzheimer's disease or attention deficit disorder; a method for the treatment of developmental disorders such as schizophrenia; Down's syndrome, Fragile X syndrome, autism or the like; a method for the treatment of behavioral disorders, e.g., anxiety, depression, or obsessive compulsive disorder; a method for the treatment of motion or motor disorders such as Parkinson's disease or epilepsy; a method for the treatment of a neurodegenerative disorder such as stroke or head trauma or withdrawal from drug addiction including addiction to nicotine, alcohol, or other substances of abuse, or any other CNS disease or disorder associated with or related to the 5-HT6 receptor.

In one embodiment, the present invention provides a method for treating attention deficit disorders (ADD, also known as Attention Deficit Hyperactivity Disorder or ADHD) in both children and adults. Accordingly, in this embodiment, the present invention provides a method for treating attention deficit disorders in a pediatric patient.

The present invention therefore provides a method for the treatment of each of the conditions listed above in a patient, preferably in a human, said method comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

In one embodiment, the invention relates to compositions comprising at least one compound of formula I, or a pharmaceutically acceptable salt thereof, and one or more pharmaceutically acceptable carriers, excipients, or diluents. Such compositions include pharmaceutical compositions for treating or controlling disease states or conditions of the central nervous system. In certain embodiments, the compositions comprise mixtures of one or more compounds of formula I.

In certain embodiments, the invention relates to compositions comprising at least one compound of formula I, or a pharmaceutically acceptable salt thereof, and one or more pharmaceutically acceptable carriers, excipients, or diluents. Such compositions are prepared in accordance with acceptable pharmaceutical procedures. Pharmaceutically acceptable carriers are those carriers that are compatible with the other ingredients in the formulation and are biologically acceptable.

The compounds of formula I may be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

In certain embodiments, a compound of formula I is provided in a disintegrating tablet formulation suitable for pediatric administration.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

In certain embodiments, a liquid pharmaceutical composition is provided wherein said composition is suitable for pediatric administration. In other embodiments, the liquid composition is a syrup or suspension.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of formula I may be administered rectally or vaginally in the form of a conventional suppository. For administration by intranasal or intrabronchial inhalation or insufflation, the compounds of formula I can be formulated into an aqueous or partially aqueous solution, which can then be utilized in the form of an aerosol. The compounds of formula I can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The therapeutically effective amount of a compound of formula I provided to a patient will vary depending upon what is being administered, the purpose of the administration, such as prophylaxis or therapy, the state of the patient, the manner of administration, and the like. In therapeutic applications, compounds of formula I are provided to a patient suffering from a condition in an amount sufficient to treat or at least partially treat the symptoms of the condition and its complications. An amount adequate to accomplish this is a "therapeutically effective amount" as described previously herein. The dosage to be used in the treatment of a specific case must be subjectively determined by the attending physician. The variables involved include the specific condition and the size, age, and response pattern of the patient. The treatment of substance abuse follows the same method of subjective drug administration under the guidance of the attending physician. Generally, a starting dose is about 5 mg per day with gradual increase in the daily dose to about 150 mg per day, to provide the desired dosage level in the patient.

In certain embodiments, the present invention is directed to prodrugs of compounds of formula I. The term "prodrug," as used herein, means a compound that is convertible in vivo by metabolic means (e.g. by hydrolysis) to a compound of formula I. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., Journal of Drug Delivery Reviews, 8:1-38(1992), Bundgaard, J. of Pharmaceutical Sciences, 77:285 et seq. (1988); and Higuchi and Stella (eds.) Prodrugs as Novel Drug Delivery Systems, American Chemical Society (1975).

For a more clear understanding, and in order to illustrate the invention more clearly, specific examples thereof are set forth hereinbelow. The following examples are merely illustrative and are not to be understood as limiting the scope and underlying principles of the invention in any way. The term HNMR designates proton nuclear magnetic resonance. The terms THF, DMF and DMSO designate tetrahydrofuran, dimethyl formamide and dimethylsulfoxide, respectively. All chromatography is performed using $SiO_2$ as support. Unless otherwise noted, all parts are parts by weight.

Example 1

Preparation of 3-(Naphthalene-1-sulfonyl)-5-(pyrrolidin-3-yloxy)-1H-indazole

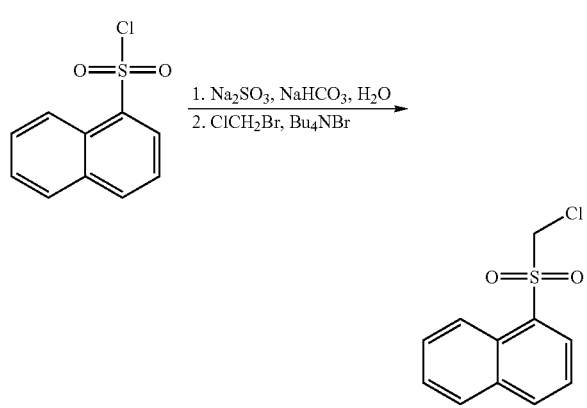

1-Chloromethanesulfonyl-naphthalene

A mixture of 1-naphthalene sulfonyl chloride (20.2 g, 89.1 mmol), sodium sulfite (22.5 g, 178 mmol) and sodium bicarbonate (15.1 g, 180 mmol) in water was stirred at 100° C. for one hour, allowed to cool to ambient temperatures for 40 minutes, treated with bromochloromethane (90 mL, 1.4 mol) and tetrabutylammonium bromide (2.87 g, 8.91 mmol), stirred at 75° C. for 14.5 hours and cooled to ambient temperatures. The phases were separated and the organic phase was concentrated in vacuo. The resultant residue was purified by flash chromatography with 100% ethyl acetate to give 1-chloromethanesulfonyl-naphthalene as a pale yellow solid, 19.0 g (88.8% yield), mp 103-5° C., Mass Spectrum (+EI, M+) m/z 240. $^1$HNMR (500 MHz, DMSO-$d_6$): δ8.64-5 (m, 1H), 8.41 (d, 1H, J=8.23 Hz), 8.27 (dd, 1H, J=7.33 Hz and 1.22 Hz), 8.16-8.18 (m, 1H), 7.71-7.81 (m, 3H), 5.40 ppm, (s, 2H). Elemental Analysis for $C_{11}H_9ClO_2S$: Calcd: C, 54.89; H, 3.77; N, 0.00; Found: C, 54.98; H, 3.81; N, 0.00.

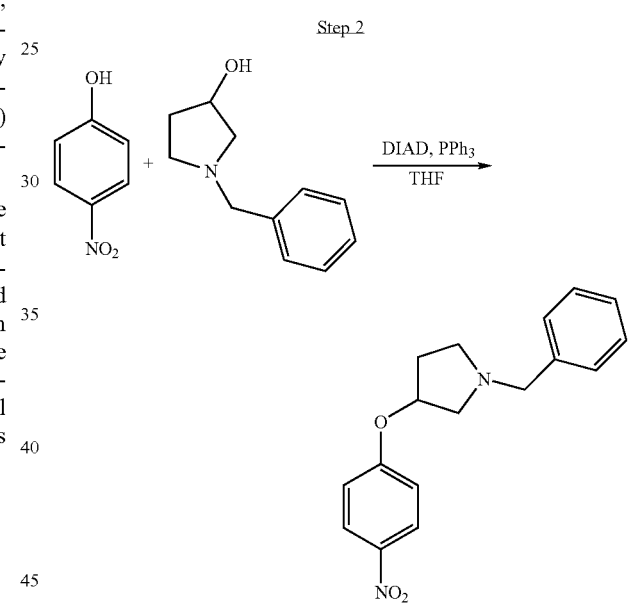

1-Benzyl-3-(4-nitro-phenoxy)-pyrrolidine

A chilled solution of 4-nitrophenol (3.9 g, 28 mmol) and 1-benzyl-3-pyrrolidinol (7.5 g, 42 mmol) in THF was treated with diisopropyl azodicarboxylate (8.3 mL, 42 mmol), stirred at ambient temperatures, under nitrogen, for 45 minutes, poured into excess water and extracted with ethyl acetate. The extracts were combined, washed with brine, dried over anhydrous magnesium sulfate and concentrated in vacuo. The resultant residue was twice purified by flash chromatography with 40% ethyl acetate in hexane to give 1-benzyl-3-(4-nitrophenoxy)-pyrrolidine as a dark yellow gum, 7.2 g (86% yield), Mass spectrum (+APPI, [M+H]+) m/z 299. $^1$HNMR (500 MHz, DMSO-$d_6$): δ8.11-8.15 (m, 2H), 7.23-7.29 (m, 4H), 7.17-7.21 (m, 1H), 7.02-7.07 (m, 2H), 4.97-5.02 (m, 1H), 3.56 (s, 1H), 2.80-2.84 (m, 1H), 2.61-2.71 (m, 2H), 2.28-2.41 (m, 2H), 1.73-1.79 ppm (m, 1H).

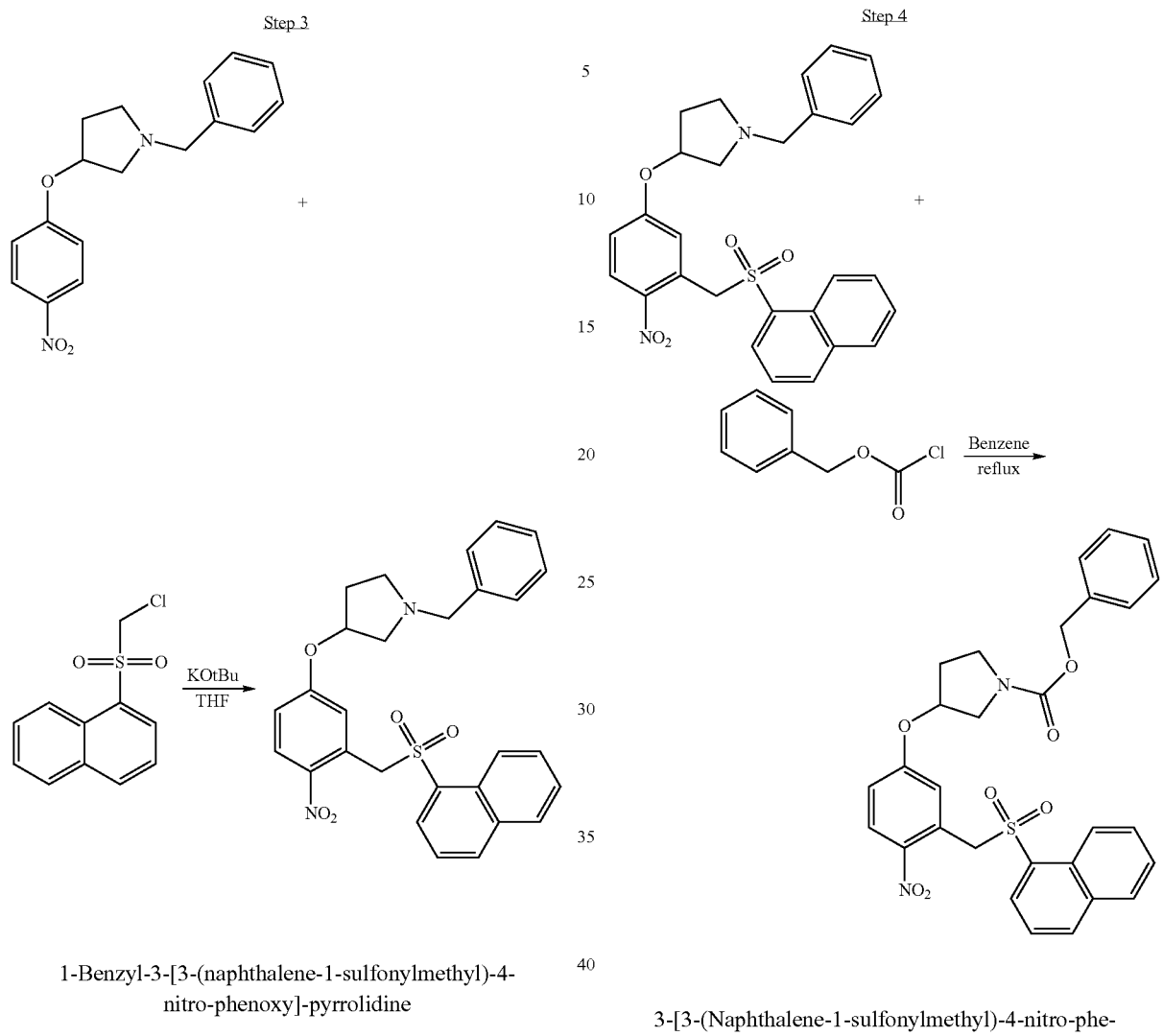

1-Benzyl-3-[3-(naphthalene-1-sulfonylmethyl)-4-nitro-phenoxy]-pyrrolidine

3-[3-(Naphthalene-1-sulfonylmethyl)-4-nitro-phenoxy]-pyrrolidine-1-carboxylic Acid Benzyl Ester A solution of 1-benzyl-3-(4-nitro-phenoxy)-pyrrolidine (7.2 g, 24 mmol) and 1-chloromethanesulfonyl-naphthalene (5.8 g, 24 mmol) in THF was chilled in an ice bath, treated dropwise with 1.0 M potassium tert-butoxide in THF (55 mL, 55 mmol), stirred at ambient temperatures for 1 hour, 10 minutes, under nitrogen, poured into water, treated with solid sodium bicarbonate and extracted with ethyl acetate. The extracts were combined, washed with brine, dried over anhydrous magnesium sulfate and concentrated in vacuo. The resultant residue was purified by flash chromatography using 40-60% ethyl acetate in hexane to give 1-benzyl-3-[3-(naphthalene-1-sulfonylmethyl)-4-nitro-phenoxy]-pyrrolidine as a brown gum/foam, 5.7 g (47.1% yield), Mass spectrum (+EI, [M+H]$^+$) m/z 503. $^1$HNMR (500 MHz, DMSO-d$_6$): δ8.44-8.46 (m, 1H), 8.27 (d, 1H, J=8.30 Hz), 8.07-8.09 (m, 1H), 7.92-7.96 (m, 2H), 7.58-7.66 (m, 3H), 7.19-7.31 (m, 5H), 6.99 (dd, 1H, J=9.15 Hz and 2.81 Hz), 6.66 (d, 1H, J=2.81 Hz), 5.24 (d, 2H, J=2.20 Hz), 4.65-4.69 (m, 1H), 3.53 (s, 2H), 2.59-2.66 (m, 2H), 2.41-2.42 (m, 1H), 2.27-2.34 (m, 1H), 2.00-2.10 (m, 1H), 1.43-1.54 ppm (m, 1H).

A solution of 1-benzyl-3-[3-(naphthalene-1-sulfonylmethyl)-4-nitro-phenoxy]-pyrrolidine (4.2 g, 8.4 mmol) and benzylchloroformate (12.0 mL, 84 mmol in 2 equal portions) in benzene was heated at reflux temperature, under nitrogen, for 3 hours, cooled to ambient temperatures, poured into 2.5 N sodium hydroxide and extracted with ethyl acetate. The extracts were combined, washed sequentially with water and brine, dried over anhydrous magnesium sulfate and concentrated in vacuo. The resultant residue was purified by flash chromatography using 40-50% ethyl acetate in hexane to afford 3-[3-(naphthalene-1-sulfonylmethyl)-4-nitro-phenoxy]-pyrrolidine-1-carboxylic acid benzyl ester as a buff foam, 3.2 g (70% yield), Mass spectrum (+EI, [M+H]$^+$) m/z 547. $^1$HNMR (500 MHz, DMSO-d$_6$): δ8.46 (d, 1H, J=7.44 Hz), 8.27 (d, 1H, J=8.06 Hz), 8.06-8.08 (m, 1H), 7.94-7.99 (m, 2H), 7.57-7.68 (m, 3H), 7.26-7.39 (m, 5H), 7.09 (dd, 1H, J=9.15 Hz and 2.68 Hz), 6.77 (s, 1H), 5.19-5.26 (m, 2H), 5.01-5.10 (m, 2H), 4.90 (s, 1H), 3.42-3.59 (m, 2H), 3.31-3.36 (m, 1H), 1.98-2.10 (m, 1H), 1.79-1.86 ppm (m, 1H).

Step 5

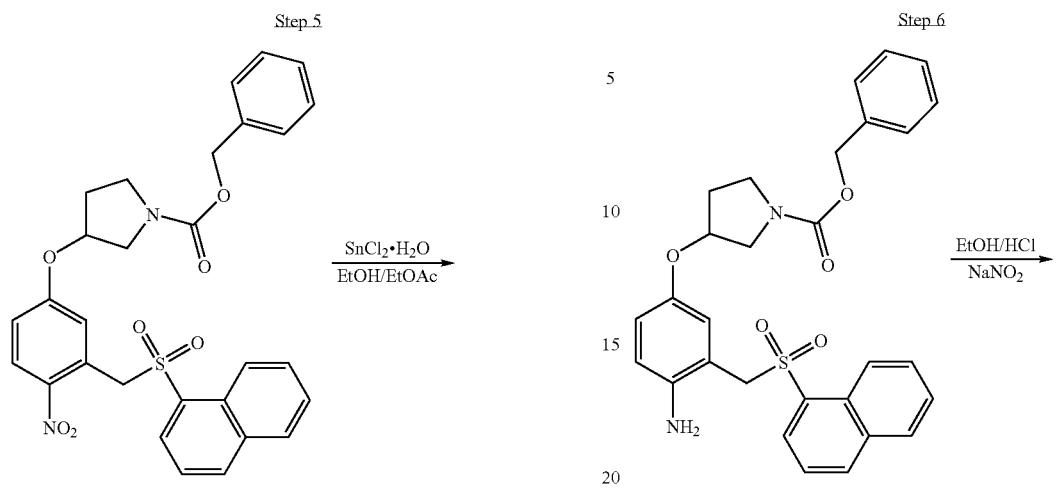

Step 6

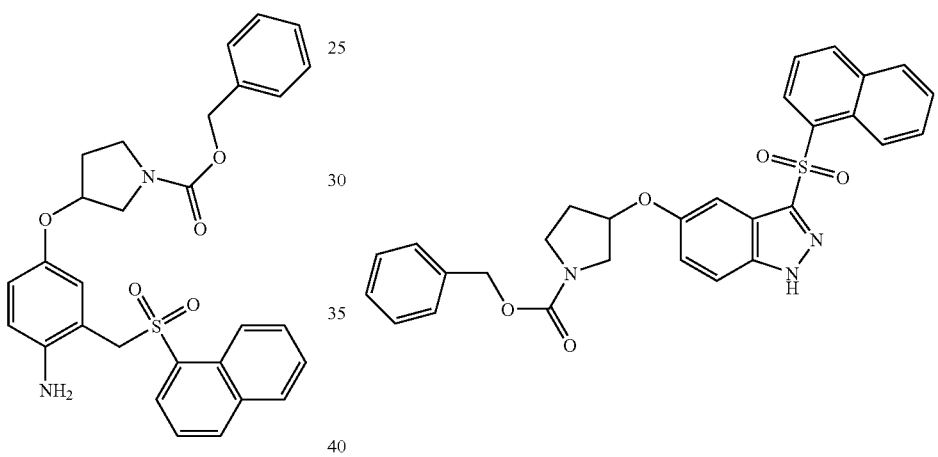

3-[3-(Naphthalene-1-sulfonyl)-1H-indazol-5-yloxy]-pyrrolidine-1-carboxylic Acid Benzyl Ester 3-[4-Amino-3-(naphthalene-1-sulfonylmethyl)-phenoxy]-pyrrolidine-1-carboxylic Acid Benzyl Ester A solution of 3-[3-(naphthalene-1-sulfonylmethyl)-4-nitro-phenoxy]-pyrrolidine-1-carboxylic acid benzyl ester (3.1 g, 5.7 mmol) in ethyl acetate was treated sequentially with ethanol and tin (II) chloride dihydrate (20.2 g, 89.5 mmol), stirred at 75° C., under nitrogen, for 2 hours, 20 minutes, poured into excess water and extracted with ethyl acetate. The combined extracts were washed sequentially with 2.5 N sodium hydroxide and brine, dried over anhydrous magnesium sulfate and concentrated in vacuo for 20 minutes at 80° C. to yield 3-[4-amino-3-(naphthalene-1-sulfonylmethyl)-phenoxy]-pyrrolidine-1-carboxylic acid benzyl ester as a yellow solid, 2.37 g (82% yield), mp 162-4° C.; Mass spectrum (+EI, [M+H]$^+$) m/z 517. $^1$HNMR (500 MHz, DMSO-d$_6$): δ8.60-8.63 (m, 1H), 8.26 (dd, 1H, J=12.81 Hz and 8.23 Hz), 8.03-8.08 (m, 2H), 7.58-7.72 (m, 3H), 7.27-7.40 (m, 5H), 6.56-6.61 (m, 2H), 6.06 (s, 1H), 5.03-5.09 (m, 2H), 4.72 (s, 2H), 4.67 (s, 2H), 4.30 (s, 1H), 3.32-3.42 (m, 2H), 3.15-3.21 (m, 2H), 1.74-1.81 (m, 1H), 1.66-1.63 ppm (m, 1H).

A suspension of 3-[4-amino-3-(naphthalene-1-sulfonylmethyl)-phenoxy]-pyrrolidine-1-carboxylic acid benzyl ester (2.36 g, 4.57 mmol) in ethanol and 1.0 N hydrochloric acid (85 mL) was heated to aid dissolution. The reaction mixture was treated slowly with sodium nitrite (0.549 g, 7.96 mmol) in water, stirred at ambient temperatures for 50 minutes, basified with solid sodium carbonate, stirred at ambient temperatures for 30 minutes and concentrated in vacuo. The resultant residue was partitioned in ethyl acetate and brine. The organic phase was dried over anhydrous magnesium sulfate and concentrated in vacuo. This residue was purified twice by flash chromatography with 2% methanol in chloroform and with 1.5-10% methanol in chloroform to afford 3-[3-(naphthalene-1-sulfonyl)-1H-indazol-5-yloxy]-pyrrolidine-1-carboxylic acid benzyl ester as a buff-colored foam, 1.69 g (70.1% yield), Mass spectrum (+EI, [M+H]$^+$) m/z 528. $^1$HNMR (500 MHz, DMSO-d$_6$): δ14.09 (s, 1H), 8.72-8.75 (m, 1H), 8.55 (d, 1H, J=7.44 Hz), 8.17-8.27 (m, 1H), 7.98-8.03 (m, 1H), 7.52-7.74 (m, 4H), 7.19-7.34 (m, 6H), 7.06 (d, 1H, J=8.78 Hz), 4.99-5.09 (m, 3H), 3.61-3.70 (m, 1H), 3.34-3.55 (m, 3H), 2.11-2.28 (m, 1H), 1.99-2.07 ppm (m, 1H).

Step 7

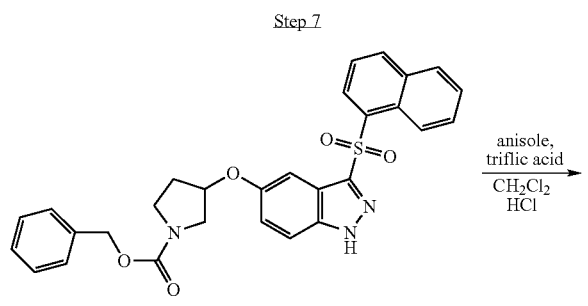

3-(Naphthalene-1-sulfonyl)-5-(pyrrolidin-3-yloxy)-1H-indazole Hydrochloride

Triflic acid (1.6 mL, 18 mmol) was added to a solution of 3-[3-(naphthalene-1-sulfonyl)-1H-indazol-5-yloxy]-pyrrolidine-1-carboxylic acid benzyl ester (1.35 g, 2.56 mmol) and anisole (0.83 mL, 7.7 mmol) in methylene chloride at 0° C. The reaction mixture was stirred at 0° C., under nitrogen, for 3.5 hours, treated with 2.5 N sodium hydroxide and extracted with warm ethyl acetate. The extracts were combined, washed with brine, dried over anhydrous magnesium sulfate and concentrated in vacuo. The resultant residue was purified by flash chromatography with 0.5-1.0% ammonium hydroxide/5.0-10% methanol in chloroform to give 3-(naphthalene-1-sulfonyl)-5-(pyrrolidin-3-yloxy)-1H-indazole as a beige solid, 0.684 g (67.7% yield), mp 168-170° C. dec. A portion of the solid (110 mg) was treated with methanol and ethereal HCl; chloroform and more methanol were then added for better solubility. The resultant mixture was concentrated to dryness in vacuo at 82° C. for 12 hours to yield the title product as a cream-colored foam (0.108 g); Mass spectrum (+EI, [M+H]$^+$) m/z 394. $^1$HNMR (500 MHz, DMSO-d$_6$): δ14.15-14.28 (br, 1H), 9.21-9.45 (br, 2H), 8.74-8.76 (m, 1H), 8.56 (dd, 1H, J=7.32 Hz and 1.22 Hz), 8.27 (d, 1H, J=8.30 Hz), 8.02-8.04 (m, 1H), 7.71-7.75 (m, 1H), 7.55-7.64 (m, 3H), 7.29 (d, 1H, J=2.20 Hz), 7.11 (dd, 1H, J=9.15 Hz and 2.31 Hz), 5.19-5.21 (m, 1H), 3.43-3.47 (m, 1H), 3.28-3.34 (m, 2H), 2.16-2.25 (m, 1H), 2.04-2.10 ppm (m, 1H).

Example 2

Preparation of 5-(1-Butyl pyrrolidin-3-yloxy)-3-(1-naphthylsulfonyl)-1H-indazole Hydrochloride

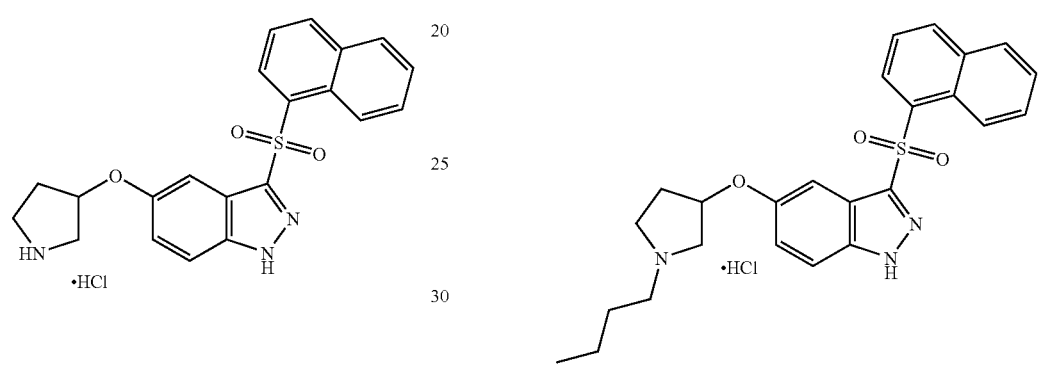

A suspension of 3-(naphthalene-1-sulfonyl)-5-(pyrrolidin-3-yloxy)-1H-indazole (52.8 mg, 0.134 mmol) in 1,2-dichloroethane was treated sequentially with butyraldehyde (0.1 mL, 1 mmol) and acetic acid (0.1 mL, 2 mmol), stirred at ambient temperatures, under nitrogen, for 20 minutes, treated with additional acetic acid (0.2 mL, 3 mmol) and 1,2-dichloroethane, stirred at ambient temperature for 1 hour, 40 minutes, treated with sodium triacetoxyborohydride (96.7 mg, 0.457 mmol), stirred for 3 hours at ambient temperatures, diluted with chloroform and poured into excess 2.5 N sodium hydroxide. The phases were separated; the organic phase was washed with brine, dried over anhydrous magnesium sulfate and concentrated in vacuo. The resultant residue was purified by flash chromatography using 0.25% ammonium hydroxide/2.5% methanol in chloroform to afford 5-(1-butyl-pyrrolidin-3-yloxy)-3-(naphthalene-1-sulfonyl)-1H-indazole as a light yellow foam, 30.0 mg (49.8% yield). The foam was dissolved in chloroform and methanol, treated with ethereal HCl and concentrated in vacuo at 83° C. for 13 hours to give the title product as a pale yellow foam, 26.9 mg, Mass spectrum (+EI, [M+H]$^+$) m/z 450. $^1$HNMR (500 MHz, DMSO-d$_6$): δ14.19 (s, 1H), 10.25-10.65 (m*, 1H), 8.75 (d, 1H, J=8.54 Hz), 8.56 (d, 1H, J=6.83 Hz), 8.28 (d, 1H, J=8.29 Hz), 8.03-8.05 (m, 1H), 7.71-7.75 (m, 1H), 7.56-7.65 (m, 3H), 7.27 (s, 1H), 7.12 (dd, 1H, J=9.15 Hz and 2.32 Hz), 5.19-5.24 (m, 1H), 3.39-3.96 (m*, 3H), 3.08-3.24 (m*, 3H), 2.00-2.63 (m*, 2H), 1.56-1.64 (m, 2H), 1.21-1.34 (m, 2H), 0.80-0.90 ppm (m, 3H). *Conformational isomers due to protonation of tertiary amine.

Example 3

Preparation of 3-(Naphthalene-1-sulfonyl)-5-(1-propyl-pyrrolidin-3-yloxy)-1H-indazole Hydrochloride

Example 4

Preparation of 5-(1-Isopropyl-pyrrolidin-3-yloxy)-3-(naphthalene-1-sulfonyl)-1H-indazole Hydrochloride

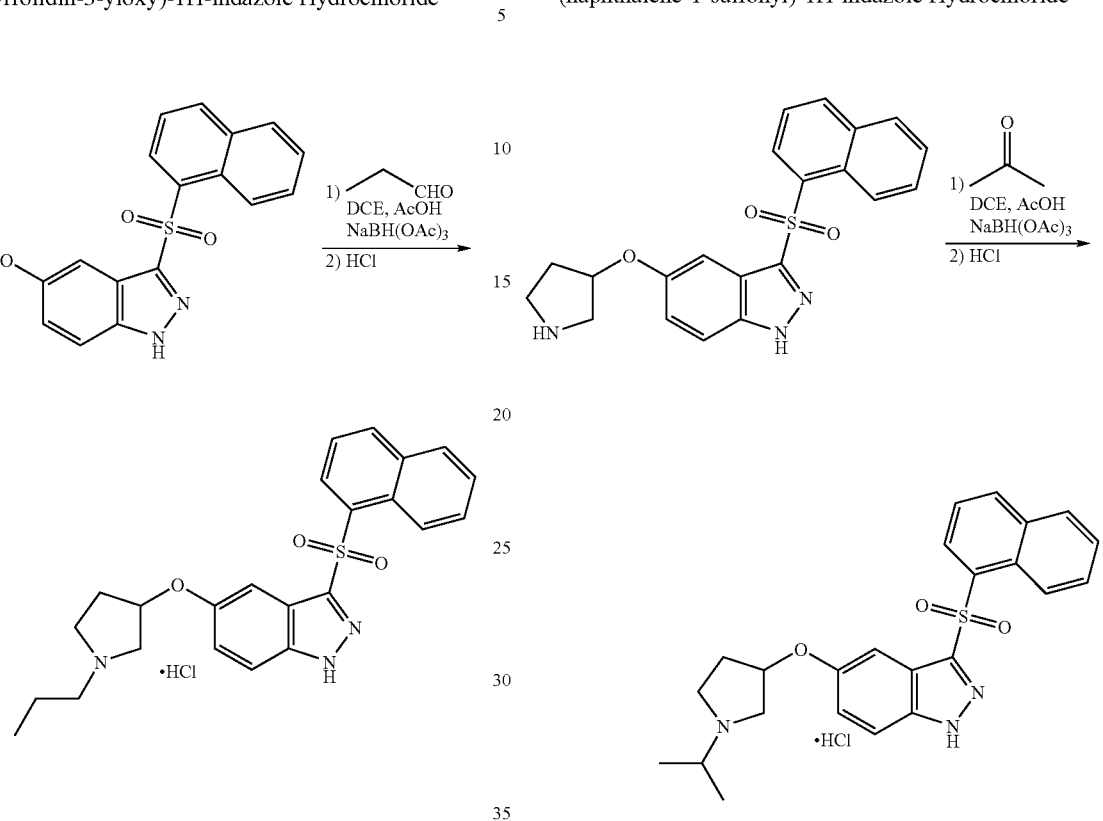

A solution of 3-(naphthalene-1-sulfonyl)-5-(pyrrolidin-3-yloxy)-1H-indazole (75.1 mg, 0.191 mmol) in methanol and chloroform was treated with ethereal HCl, concentrated, treated sequentially with 32 mL of 1,2-dichloroethane, propionaldehyde (0.55 mL, 7.6 mmol in two portions) and acetic acid (0.55 mL, 9.6 mmol in two portions). The reaction mixture was stirred, under nitrogen, at ambient temperatures for 2.5-3 hours, treated with sodium triacetoxyborohydride (81.2 mg, 0.384 mmol), stirred 1.5-20 hours, diluted with chloroform and washed with 1.0 N sodium hydroxide and brine. (Methanol was added to the organic phase to aid in solubility.) The organic phase was dried over magnesium sulfate and concentrated in vacuo. The resultant residue was purified by flash chromatography using 0.3-0.8% ammonium hydroxide/3.0-8.0% methanol in chloroform to yield 3-(naphthalene-1-sulfonyl)-5-(1-propyl-pyrrolidin-3-yloxy)-1H-indazole as a light yellow foam (43.8 mg, 52.5%). The foam was dissolved in methanol and chloroform, treated with isopropanolic HCl and concentrated in vacuo at 86° C. for 13 hours to give the title product as a light beige foam, 43.7 mg, Mass spectrum (+EI, [M+H]$^+$) m/z 436. $^1$HNMR (500 MHz, DMSO-d$_6$): δ14.20 (s, 1H), 10.29-10.62 (m*, 1H), 8.74 (d, 1H, J=8.54 Hz), 8.56 (d, 1H, J=6.95 Hz), 8.28 (d, 1H, J=8.30 Hz), 8.03-8.05 (m, 1H), 7.71-7.75 (m, 1H), 7.56-7.65 (m, 3H), 7.27 (s, 1H), 7.12 (dd, 1H, J=9.15 Hz and 2.32 Hz), 5.17-5.23 (m, 1H), 3.30-3.95 (m*, 3H), 3.11-3.23 (m*, 3H), 2.01-2.56 (m*, 2H), 1.60-1.69 (m, 2H), 0.87-0.90 ppm (m, 3H). *Conformational isomers due to protonation of tertiary amine.

A suspension of 3-(naphthalene-1-sulfonyl)-5-(pyrrolidin-3-yloxy)-1H-indazole (59.8 mg, 0.152 mmol) in 1,2-dichloroethane was treated with acetone (0.1 mL, 1 mmol) and acetic acid (0.1 mL, 2 mmol), stirred for one hour at ambient temperatures, under nitrogen, treated with sodium triacetoxyborohydride (66.3 mg, 0.313 mmol), stirred for 4 hours, diluted with chloroform and washed sequentially with 1.0 N sodium hydroxide and brine, treated with methanol to aid in solubility, dried over anhydrous magnesium sulfate and concentrated in vacuo. The resultant residue was purified by flash chromatography using 0.2% ammonium hydroxide/2.0% methanol in chloroform to afford 5-(1-isopropyl-pyrrolidin-3-yloxy)-3-(naphthalene-1-sulfonyl)-1H-indazole as a very light yellow foam, 45.4 mg (68.6% yield). The foam was dispersed in methanol and chloroform, treated with isopropanolic HCL and concentrated in vacuo at 84° C. for 14 hours to give the title product as a light brown foam, 42.1 mg, Mass spectrum (+APPI, [M+H]$^+$) m/z 436. $^1$HNMR (500 MHz, DMSO-d$_6$): δ14.22 (d, 1H, J=4.76 Hz), 10.39-11.06 (m*, 1H), 8.75 (d, 1H, J=8.66 Hz), 8.55-8.59 (m, 1H), 8.27 (d, 1H, J=8.18 Hz), 8.04 (d, 1H, J=7.93 Hz), 7.71-7.75 (m, 1H), 7.56-7.64 (m, 3H), 7.25-7.28 (m, 1H), 7.09-7.15 (m, 1H), 5.19-5.22 (m, 1H), 3.39-3.87 (m*, 4H), 3.20-3.25 (m*, 1H), 2.02-2.53 (m, 2H), 1.24-1.28 ppm (m, 6H). *Conformational isomers due to protonation of tertiary amine.

Example 5

Preparation of 5-(1-Methyl-pyrrolidin-3-yloxy)-3-(naphthalene-1-sulfonyl)-1H-indazole Hydrochloride

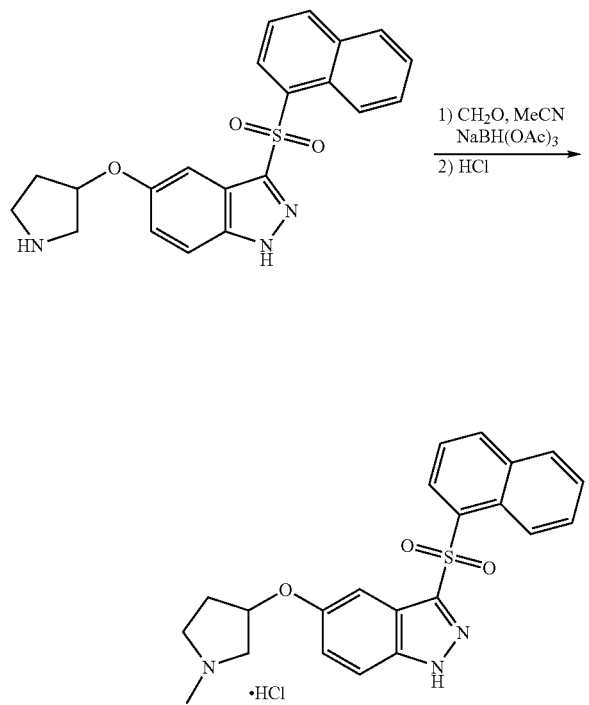

A solution of 3-(naphthalene-1-sulfonyl)-5-(pyrrolidin-3-yloxy)-1H-indazole (73.4 mg, 0.187 mmol) in $CH_3CN$ was treated with 37% aqueous formaldehyde (0.15 mL, 2.0 mmol) and sodium triacetoxyborohydride (92.1 mg, 0.435 mmol), stirred for 3 hours at ambient temperatures and partitioned in chloroform and 1.0 N sodium hydroxide. The phases were separated; the organic phase was washed with brine, treated with methanol to aid in solubility, dried over anhydrous magnesium sulfate and concentrated in vacuo. The resultant residue was purified by flash chromatography using 0.3% ammonium hydroxide/3.0% methanol in chloroform to give 5-(1-methyl-pyrrolidin-3-yloxy)-3-(naphthalene-1-sulfonyl)-1H-indazole as a light orange foam, 28.8 mg (37.9% yield). The foam was taken up in methanol and chloroform, treated with isopropanolic HCl and concentrated in vacuo at 84° C. for 14 hours to yield the title product as a light orange foam, 27.2 mg, Mass spectrum (+EI, $[M+H]^+$) m/z 408. $^1$HNMR (500 MHz, DMSO-$d_6$): δ14.20 (s, 1H), 10.38-10.60 (br, 1H), 8.74 (d, 1H, J=8.66 Hz), 8.54-8.56 (m, 1H), 8.28 (d, 1H, J=8.30 Hz), 8.03-8.05 (m, 1H), 7.71-7.75 (m, 1H), 7.56-7.65 (m, 3H), 7.28 (d, 1H, J=2.20 Hz), 7.12 (dd, 1H, J=9.15 Hz and 2.32 Hz), 5.22 (s, 1H), 3.31-3.74 (m*, 3H), 2.85 (s, 3H), 2.03-2.12 ppm (m, 1H). *Conformational isomers due to protonation of tertiary amine.

Example 6

Preparation of 3-(1-Naphthylsulfonyl)-5-(piperidin-4-yloxy)-1H-indazole Hydrochloride

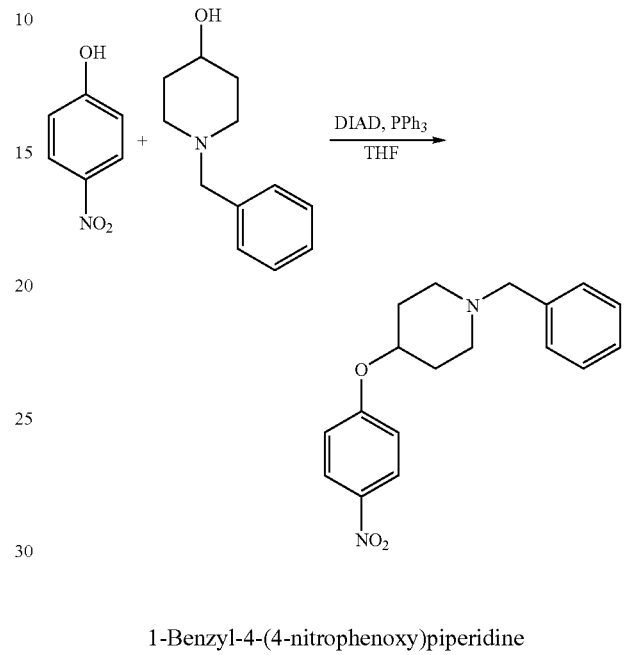

1-Benzyl-4-(4-nitrophenoxy)piperidine

A chilled solution of 4-nitrophenol (1.14 g, 8.12 mmol), triphenyl phosphine (3.21, 12.2 mmol) and 1-benzyl-4-hydroxypiperidine (2.6 g, 14 mmol) in THF was treated with diisopropyl azodicarboxylate (DIAD) (2.4 mL, 12 mmol), stirred at ambient temperatures, under nitrogen, for 17.5 hours, poured into excess water and extracted with ethyl acetate. The extracts were combined, washed with brine, dried over anhydrous magnesium sulfate and concentrated in vacuo. The resultant residue was purified by flash chromatography with 30-40% ethyl acetate in hexane to give 1-benzyl-4-(4-nitro-phenoxy)-piperidine as a yellow semi-solid, 0.880 g (35% yield); Mass spectrum (+EI, $[M+H]^+$) m/z 313. $^1$HNMR (500 MHz, DMSO-$d_6$): δ8.11-8.15 (m, 2H), 7.24-7.30 (m, 4H), 7.18-7.22 (m, 1H), 7.10-7.14 (m, 2H), 4.53-4.59 (m, 1H), 3.45 (s, 2H), 2.60-2.64 (m, 2H), 2.20-2.26 (m, 2H), 1.91-1.95 (m, 2H), 1.58-1.67 ppm (m, 2H).

Step 2

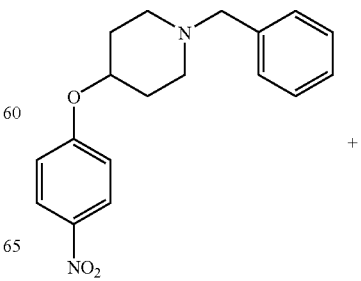

+

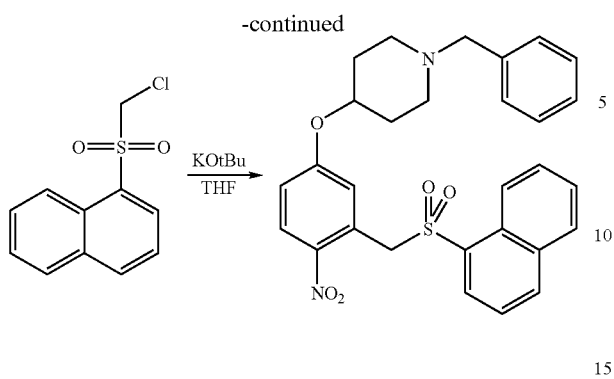
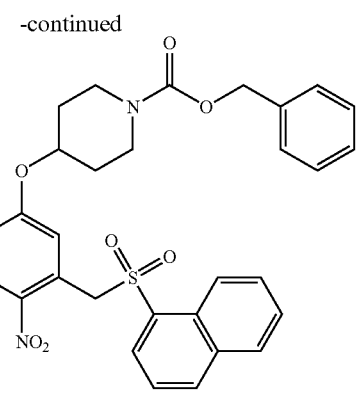

1-Benzyl-4-[3-(1-naphthylsulfonylmethyl)-4-nitro-phenoxy]piperidine

A solution of 1-benzyl-4-(4-nitrophenoxy)piperidine (3.00 g, 9.60 mmol) and 1-chloromethanesulfonyl-naphthalene (2.35 g, 9.76 mmol) in THF was chilled in an ice bath, treated dropwise with 1.0 M potassium tert-butoxide in THF (20 mL, 20 mmol), stirred at ambient temperature for 1 hour, 20 minutes under nitrogen, poured into water and extracted with ethyl acetate. The extracts were combined, washed with brine, dried over anhydrous magnesium sulfate and concentrated in vacuo. The resultant residue was purified by flash chromatography using 40-80% ethyl acetate in hexane to give 1-benzyl-4-[3-(naphthalene-1-sulfonylmethyl)-4-nitro-phenoxy]-piperidine as a brown gum/foam, 2.36 g (47.6% yield); Mass spectrum (+EI, [M+H]$^+$) m/z 517. $^1$HNMR (500 MHz, DMSO-d$_6$): δ8.44-8.47 (m, 1H), 8.28 (d, 1H, J=8.17 Hz), 8.06-8.09 (m, 1H), 7.91-7.96 (m, 2H), 7.59-7.68 (m, 3H), 7.20-7.32 (m, 5H), 7.03 (dd, 1H, J=9.15 Hz and 2.80 Hz), 6.62 (d, 1H, J=2.81 Hz), 5.24 (s, 2H), 4.07-4.10 (m, 1H), 3.44 (s, 2H), 2.49-2.53 (m, 2H), 2.05-2.09 (m, 2H), 1.65-1.69 (m, 2H), 1.38-1.46 ppm (m, 2H).

Step 3

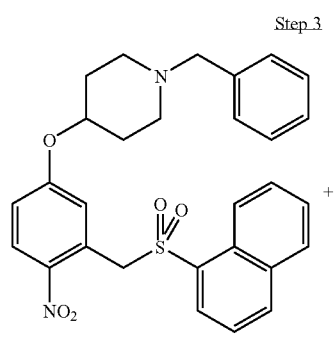

+

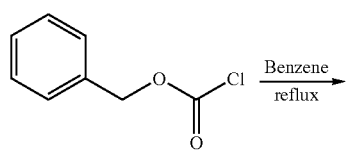

4-[3-(1-Naphthylsulfonylmethyl)-4-nitrophenoxy] piperidin-1-ylcarboxylic Acid Benzyl Ester A solution of 1-benzyl-4-[3-(1-naphthylsulfonylmethyl)-4-nitrophenoxy]-piperidine (4.7 g, 9.1 mmol) and benzylchloroformate (6.0 mL, 42 mmol) in benzene was heated at reflux temperature, under nitrogen, for 3 hours, cooled to ambient temperatures, poured into 2.5 N sodium hydroxide and extracted with ethyl acetate. The extracts were combined, washed with water and brine, dried over anhydrous magnesium sulfate and concentrated in vacuo. The resultant residue was purified by flash chromatography using 30-50% ethyl acetate in hexane to afford 4-[3-(naphthalene-1-sulfonylmethyl)-4-nitro-phenoxy]-piperidine-1-carboxylic acid benzyl ester as a buff foam/amber gum, 3.9 g, 76%); Mass spectrum (+EI, [M+H]$^+$) m/z 561. $^1$HNMR (500 MHz, DMSO-d$_6$): δ8.44-8.46 (m, 1H), 8.30 (d, 1H, J=8.17 Hz), 8.07-8.10 (m, 1H), 7.94-7.99 (m, 2H), 7.61-7.68 (m, 3H), 7.27-7.37 (m, 5H), 7.09 (dd, 1H, J=9.15 Hz and 2.81 Hz), 6.72 (d, 1H, J=2.81 Hz), 5.23 (s, 2H), 5.05 (s, 2H), 4.36-4.40 (m, 1H), 3.58-3.61 (m, 2H), 3.10-3.20 (m, 2H), 1.70-1.74 (m, 2H), 1.34-1.42 ppm (m, 2H).

Step 4

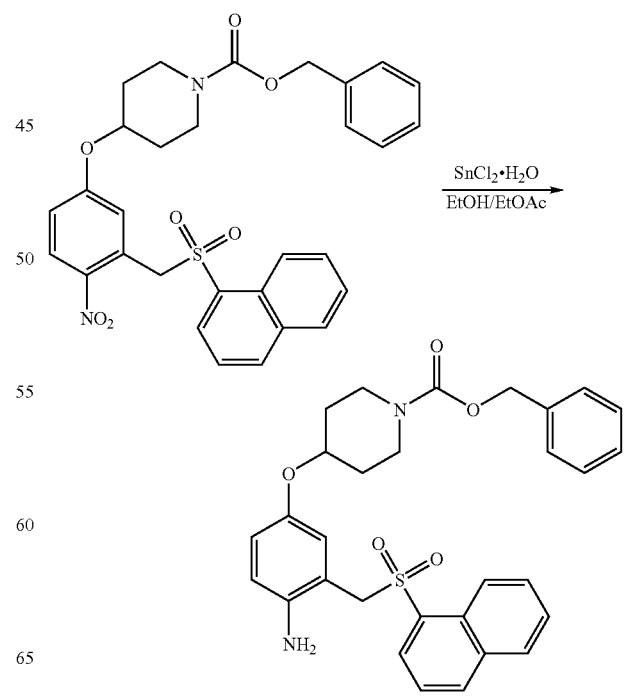

4-[4-Amino-3-(1-naphthylsulfonylmethyl)phenoxy]-piperidin-1-ylcarboxylic Acid Benzyl Ester A solution of 4-[3-(1-naphthylsulfonylmethyl)-4-nitrophenoxy]piperidin-1-ylcarboxylic acid benzyl ester (3.90 g, 6.96 mmol) in ethyl acetate was treated sequentially with ethanol and tin (II) chloride dihydrate (24.0 g, 106 mmol), stirred at 75° C. under nitrogen for 3 hours and concentrated in vacuo. The resultant residue was partitioned in ethyl acetate and water. The phases were separated; the organic phase was washed with 2.5 N sodium hydroxide and brine, dried over anhydrous magnesium sulfate and concentrated in vacuo for 20 minutes at 78° C. to yield 4-[4-amino-3-(naphthalene-1-sulfonylmethyl)-phenoxy]-piperidine-1-carboxylic acid benzyl ester as a dark yellow film, 3.3 g (89% yield), Mass spectrum (+EI, [M+H]$^+$) m/z 531. $^1$HNMR (500 MHz, DMSO-d$_6$): δ8.57 (d, 1H, J=8.54 Hz), 8.24 (d, 1H, J=8.17 Hz), 8.03-8.06 (m, 1H), 8.00 (dd, 1H, J=7.44 Hz and 1.22 Hz), 7.58-7.69 (m, 3H), 7.27-7.38 (m, 5H), 6.53-6.58 (m, 2H), 5.97 (d, 1H, J=2.56 Hz), 5.04 (s, 2H), 4.71 (s, 2H), 4.64 (s, 2H), 3.61-3.66 (m, 1H), 3.47-3.53 (m, 2H), 2.99-3.05 (m, 2H), 1.43-1.48 (m, 2H), 1.10-1.19 ppm (m, 2H).

Step 5

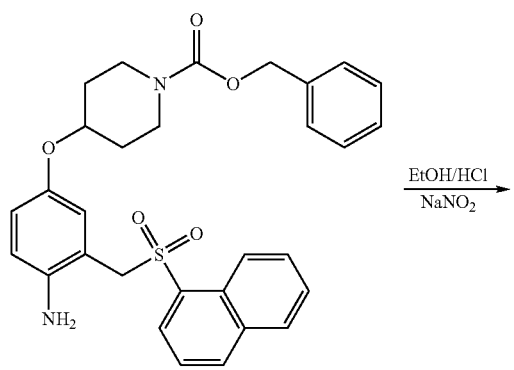

EtOH/HCl
NaNO$_2$
→

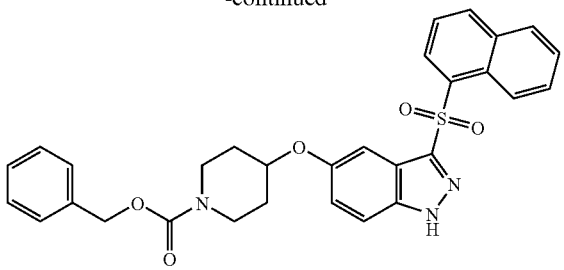

4-[3-(1-Naphthylsulfonyl)-1H-indazol-5-yloxy]piperidin-1-ylcarboxylic Acid Benzyl Ester A suspension of 4-[4-amino-3-(1-naphthylsulfonylmethyl)phenoxy]piperidin-1-ylcarboxylic acid benzyl ester (3.2 g, 6.0 mmol) in ethanol and 1.0 N HCl (155 mL) was heated to aid dissolution, treated slowly with sodium nitrite (0.67 g, 9.7 mmol) in water, stirred at ambient temperatures for one hour, basified with solid sodium carbonate, stirred at ambient temperature for 1 hour and concentrated in vacuo. The resultant residue was partitioned in ethyl acetate and brine. The phases were separated; the organic phase was dried over anhydrous magnesium sulfate and concentrated in vacuo. This residue was purified by flash chromatography with 35-40% ethyl acetate in hexane and 100% ethyl acetate to give 4-[3-(1-naphthylsulfonyl)-1H-indazol-5-yloxy]piperidin-1-ylcarboxylic acid benzyl ester as a light orange foam, 1.79 g (55.9% yield), Mass spectrum (+EI, [M+H]$^+$) m/z 542. $^1$HNMR (500 MHz, DMSO-d$_6$): δ14.07 (s, 1H), 8.71-8.73 (m, 1H), 8.55 (dd, 1H, J=7.45 Hz and 1.22 Hz), 8.26 (d, 1H, J=8.29 Hz), 8.01-8.03 (m, 1H), 7.70-7.74 (m, 1H), 7.51-7.62 (m, 3H), 7.27-7.35 (m, 5H), 7.23 (d, 1H, J=2.20 Hz), 7.09 (dd, 1H, J=9.03 Hz and 2.32 Hz), 5.06 (s, 2H), 4.59-4.61 (m, 1H), 3.63-3.72 (m, 2H), 3.29-3.33 (m, 2H), 1.83-1.88 (m, 2H), 1.50-1.55 ppm (m, 2H Step 6

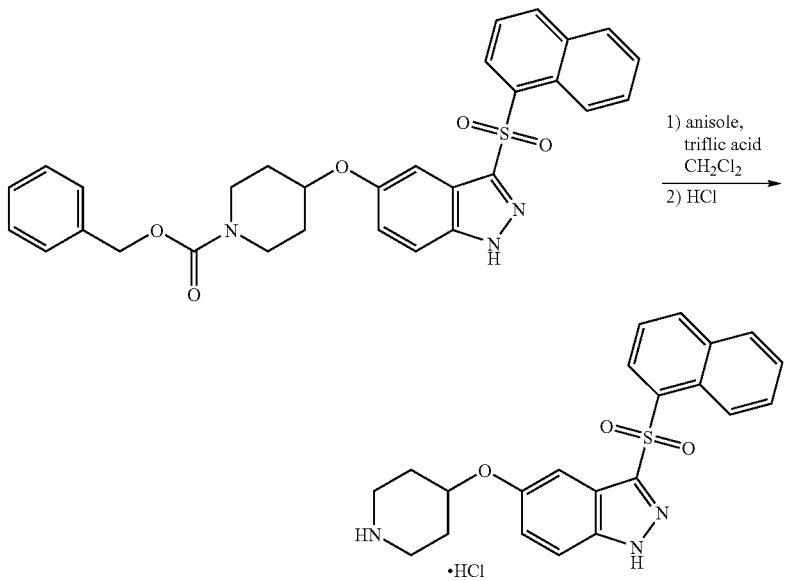

1) anisole, triflic acid CH$_2$Cl$_2$
2) HCl
→

3-(1-Naphthylsulfonyl)-5-(piperidin-4-yloxy)-1H-indazole Hydrochloride

A solution of 4-[3-(1-naphthylsulfonyl)-1H-indazol-5-yloxy]piperidin-1-ylcarboxylic acid benzyl ester (1.78 g, 3.29 mmol) and anisole (1.1 mL, 9.9 mmol) in methylene chloride at 0° C. was treated with triflic acid (2.05 mL, 23.2 mmol), stirred at 0° C. under nitrogen for 1.5 hours, treated with 2.5 N sodium hydroxide and extracted with warm ethyl acetate. The extracts were combined, washed with brine, dried over anhydrous magnesium sulfate and concentrated in vacuo. The resultant residue was purified by flash chromatography with 0.5-0.75% ammonium hydroxide/5.0-7.5% methanol in chloroform to give 3-(1-naphthylsulfonyl)-5-(piperidin-4-yloxy)-1H-indazole as a dark orange semi-solid, 0.860 g, (64.2% yield). A portion of the semi-solid (160 mg) was dispersed in methanol and chloroform, treated with ethereal HCl and concentrated in vacuo for 12 hours at 82° C. to yield the title product as a light orange solid, 0.151 g, mp 174-6° C. (dec), Mass spectrum (+EI, [M+H]$^+$) m/z 408. $^1$HNMR (500 MHz, DMSO-d$_6$): δ14.11-14.19 (br, 1H), 8.66-8.80 (br, m, 3H), 8.55-8.57 (m, 1H), 8.27 (d, 1H, J=8.30 Hz), 8.02-8.04 (m, 1H), 7.70-7.73 (m, 1H), 7.54-7.63 (m, 3H), 7.31 (d, 1H, J=2.07 Hz), 7.12-7.15 (m, 1H), 4.69-4.73 (m, 1H), 3.19-3.29 (m, 2H), 3.06-3.13 (m, 2H), 2.02-2.07 (m, 2H), 1.75-1.83 ppm (m, 2H).

Examples 7-18

Preparation of 3-(Arylsulfonyl)-5-(piperidin-4-yloxy)-1H-indazole Hydrochloride Compounds

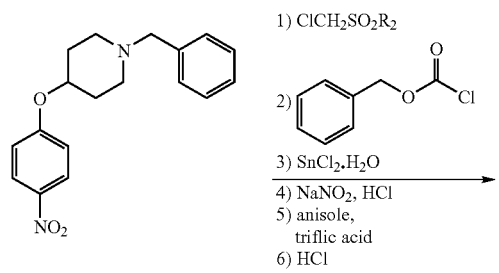

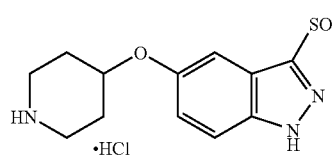

Using essentially the same procedure described in Example 6 and employing the desired chloromethylsulfonyl reagent in step 1, the compounds shown on Table I were obtained and identified by HNMR and mass spectral analyses.

TABLE I

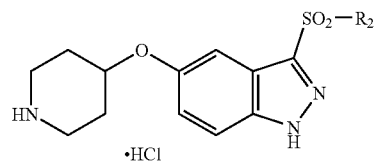

| Example No. | R2 | [M + H] |
|---|---|---|
| 7 | phenyl | 358 |
| 8 | 3-fluorophenyl | 376 |
| 9 | 2-chlorophenyl | 392 |
| 10 | 3-chlorophenyl | 392 |
| 11 | 4-chlorophenyl | 392 |
| 12 | 3-methylphenyl | 372 |
| 13 | 3-methoxyphenyl | 388 |
| 14 | 4-methoxyphenyl | 388 |
| 15 | 3-(trifluoromethyl)phenyl | 426 |
| 16 | 4-(trifluoromethyl)phenyl | 426 |
| 17 | 4-isopropylphenyl | 400 |
| 18 | 4-methylnaphth-1-yl | 422 |

Example 19

Preparation of 3-(1-Naphthylsulfonyl)-5-(1-propylpiperidin-4-yloxy)-1H-indazole Hydrochloride

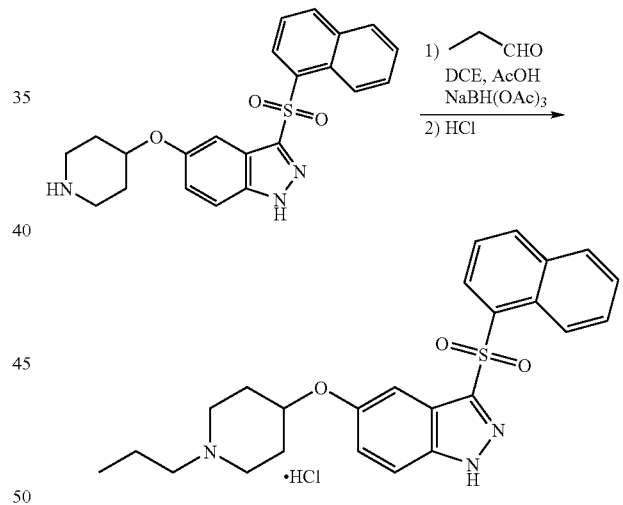

A suspension of 3-(1-naphthylsulfonyl)-5-(piperidin-4-yloxy)-1H-indazole (56.0 mg, 0.137 mmol) in 1,2-dichloroethane was treated sequentially with propionaldehyde (0.01 mL, 0.1 mmol) in 1,2-dichloroethane and acetic acid (0.1 mL, 2 mmol), stirred at ambient temperatures under nitrogen for 2 hours, treated with additional propionaldehyde (0.1 mL, 1 mmol) to aid in solubility, stirred at ambient temperatures for 1.5 hours, treated with sodium triacetoxyborohydride (59.8 mg, 0.283 mmol), stirred for 1.25 hours at ambient temperatures, diluted with ethyl acetate and poured into excess 1.0 N sodium hydroxide. The phases were separated. The organic phase was washed with brine, dried over anhydrous magnesium sulfate, and concentrated in vacuo at 81° C. for 20 minutes to yield 3-(1-naphthylsulfonyl)-5-(1-propylpiperidin-4-yloxy)-1H-indazole as a light orange solid, 50.4 mg (81.8% yield). The solid was dissolved in chloroform and methanol, treated with ethereal HCl and concentrated in vacuo at 82° C. for 15 hours to give the title product as a light orange semi-solid, 40.2 mg, Mass spectrum (+EI, [M+H]+) m/z 450. ¹HNMR (500 MHz, DMSO-$d_6$): δ14.16 (d, 1H, J=3.78 Hz), 9.97-10.10 (m*, 1H), 8.70-8.76 (m, 1H), 8.55 (dd, 1H, J=7.44 Hz and 1.22 Hz), 8.26-8.28 (m, 1H), 8.02-8.04 (m, 1H), 7.70-7.75 (m, 1H), 7.54-7.63 (m, 3H), 7.27-7.37 (s* and s*, 1H), 7.08-7.20 (dd* and m*, 1H, J=9.03 Hz and 2.08 Hz), 4.59-4.80 (m*, 1H), 3.50-3.53 (m, 1H), 3.31-3.34 (m, 1H), 2.97-3.19 (m, 4H), 2.08-2.15 (m, 2H), 1.96-2.00 (m, 1H), 1.80-1.90 (m, 1H), 1.63-1.72 (m, 2H), 0.86-0.91 ppm (m, 3H). *Conformational isomers due to protonation of tertiary amine.

Example 20

Preparation of 5-(1-Butylpiperidin-4-yloxy)-3-(1-naphthylsulfonyl)-1H-indazole Hydrochloride

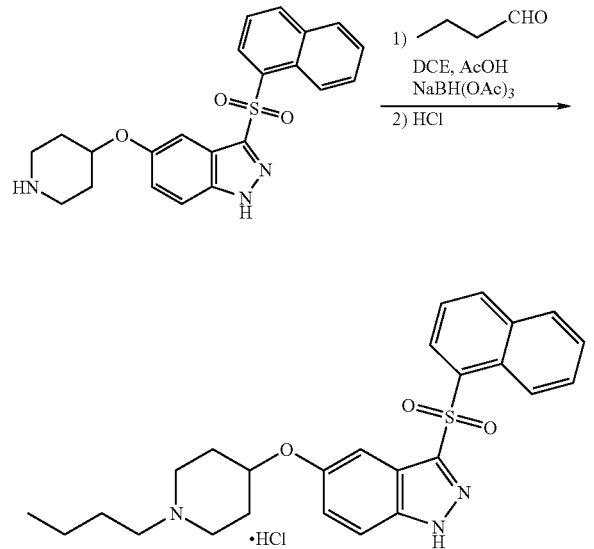

A suspension of 3-(1-naphthylsulfonyl)-5-(piperidin-4-yloxy)-1H-indazole (56.5 mg, 0.138 mmol) in 1,2-dichloroethane was treated sequentially with butyraldehyde (0.1 mL, 1 mmol) and acetic acid (0.1 mL, 2 mmol), stirred at ambient temperature for 3 hours, treated with sodium triacetoxyborohydride (46.5 mg, 0.220 mmol), stirred for 1 hour, 20 minutes under nitrogen at ambient temperatures, diluted with chloroform and poured into excess 1.0 N sodium hydroxide. The phases were separated. The organic phase was washed with brine, dried over anhydrous magnesium sulfate, and concentrated in vacuo. The resultant residue was twice purified by flash chromatography using 0.25-0.5% ammonium hydroxide/2.5-5.0% methanol in chloroform to afford 5-(1-butylpiperidin-4-yloxy)-3-(1-naphthylsulfonyl)-1H-indazole as a light orange foam, 25.6 mg (40.0% yield). The foam was dispersed in methanol, treated with ethereal HCl and concentrated in vacuo at 83° C. for 25 hours to give the title product as an orange foam, 22.0 mg, Mass spectrum (+EI, [M+H]⁺) m/z 464. ¹HNMR (500 MHz, DMSO-$d_6$): δ14.16 (d, 1H, J=4.15 Hz), 9.86-9.98 (m*, 1H), 8.73 (dd, 1H, J=15.74 Hz and 8.42 Hz), 8.54-8.56 (m, 1H), 8.27 (d, 1H, J=8.29 Hz), 8.02-8.05 (m, 1H), 7.70-7.75 (m, 1H), 7.54-7.63 (m, 3H), 7.28-7.38 (s* and s*, 1H), 7.09-7.20 (m*, 1H), 4.60-4.80 (m*, 1H), 3.52-3.55 (m, 1H), 3.32-3.35 (m, 1H), 3.00-3.16 (m, 4H), 2.06-2.16 (m, 2H), 1.97-2.00 (m, 1H), 1.79-1.88 (m, 1H), 1.60-1.67 (m, 2H), 1.25-1.34 (m, 2H), 0.92-0.87 ppm (m, 3H). *Conformational isomers due to protonation of tertiary amine.

Example 21

Preparation of 5-(1-Methylpiperidin-4-yloxy)-3-(1-naphthylsulfonyl)-1H-indazole Hydrochloride

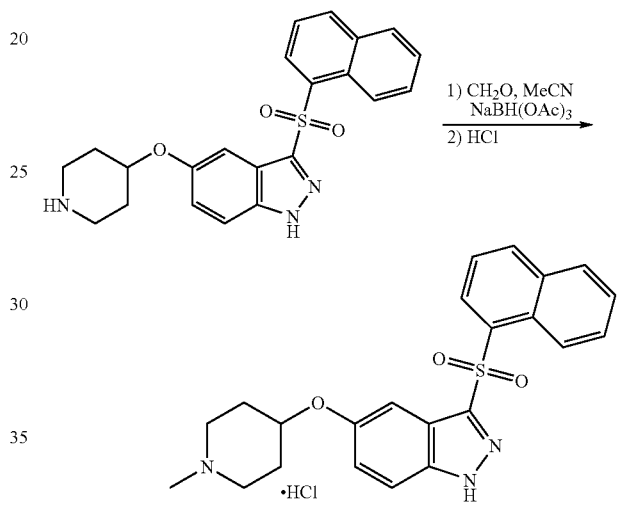

A suspension of 3-(1-naphthylsulfonyl)-5-(piperidin-4-yloxy)-1H-indazole (57.7 mg, 0.142 mmol) in acetonitrile was treated in three portions with odium triacetoxyborohydride (54 mg, 0.26 mmol) and 37% formaldehyde in water (0.1 mL, 1.3 mmol), stirred at ambient temperatures for 2.5 hours and poured into excess chloroform and 1.0 N sodium hydroxide. The phases were separated. The organic phase was washed with brine, dried over anhydrous magnesium sulfate and concentrated in vacuo. The resultant residue was purified by flash chromatography with 0.5% ammonium hydroxide/5.0% methanol in chloroform to give 5-(1-methylpiperidin-4-yloxy)-3-(1-naphthylsulfonyl)-1H-indazole (47.9 mg, 0.144 mmol) as a light orange foam. The foam was dispersed in methanol and chloroform, treated with isopropanolic HCl and concentrated in vacuo at 82° C. in for 10 hours to yield the title product as a light orange solid, mp 252-4° C.; Mass spectrum (+EI, [M+H]⁺) m/z 422. ¹HNMR (300 MHz, DMSO-$d_6$): δ14.16 (s, 1H), 10.06-10.17 (m*, 1H), 8.73-8.75 (m, 1H), 8.54-8.56 (m, 1H), 8.26-8.28 (m, 1H), 8.02-8.05 (m, 1H), 7.72 (t, 1H, J=7.81 Hz), 7.55-7.63 (m, 3H), 7.29-7.37 (m*, 1H), 7.10-7.20 (m*, 1H), 4.58-4.77 (m*, 1H), 3.45-3.50 (m, 1H), 3.07-3.20 (m, 2H), 2.75 (s, 3H), 1.70-2.20 ppm (m*, 4H). *Conformational isomers due to protonation of tertiary amine.

Example 22

Preparation of 5-(1-Isopropylpiperidin-4-yloxy)-3-(1-naphthylsulfonyl)-1H-indazole Hydrochloride

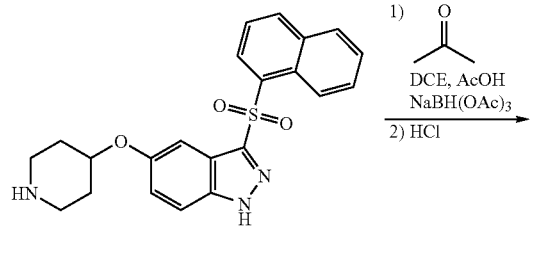

A suspension of 3-(1-naphthylsulfonyl)-5-(piperidin-4-yloxy)-1H-indazole (71.2 mg, 0.175 mmol) in 1,2-dichloroethane was treated sequentially with acetone (0.4 mL, 5 mmol) and acetic acid (0.13 mL, 2.3 mmol), stirred for 2 hours, treated portionwise with sodium triacetoxyborohydride (255 mg, 1.20 mmol), stirred for 25 hours at ambient temperatures under nitrogen, diluted with ethyl acetate and washed with 1.0 N sodium hydroxide and brine. The organic phase was treated with methanol and chloroform, dried over anhydrous magnesium sulfate and concentrated in vacuo. The resultant residue was purified by flash chromatography using 0.3-1.0% ammonium hydroxide/3.0-10% methanol in chloroform to afford 5-(1-isopropylpiperidin-4-yloxy)-3-(1-naphthylsulfonyl)-1H-indazole as a light orange foam, 40.9 mg (52.0% yield). The foam was dispersed in methanol and chloroform, treated with isopropanolic HCl and concentrated for 12 hours in vacuo to yield the title product as a light orange foam, 37 mg, Mass spectrum (−EI, [M−H]⁻) m/z 448. $^1$HNMR (300 MHz, DMSO-$d_6$): δ14.11-14.15 (m*, 1H), 9.82-9.84 (m, 1H), 8.69-8.76 (m, 1H), 8.54-8.58 (m, 1H), 8.27 (d, 1H, J=8.30 Hz), 8.02-8.04 (m, 1H), 7.70-7.75 (m, 1H), 7.54-7.63 (m, 3H), 7.29-7.36 (m*, 1H), 7.07-7.21 (m* and dd*, 1H, J=9.15 Hz and 2.31 Hz), 4.60-4.81 (m*, 1H), 3.40-3.50 (m, 2H), 3.06-3.21 (m*, 3H), 2.10-2.20 (m, 2H), 2.00-2.08 (m, 1H), 1.80-1.95 (m, 1H), 1.22-1.28 ppm (m, 6H). *Conformational isomers due to protonation of tertiary amine.

Example 23

Preparation of 3-(1-Naphthylsulfonyl)-5-{[1-(2-phenylethyl)piperidin-4-yl]oxy}-1H-indazole Hydrochloride

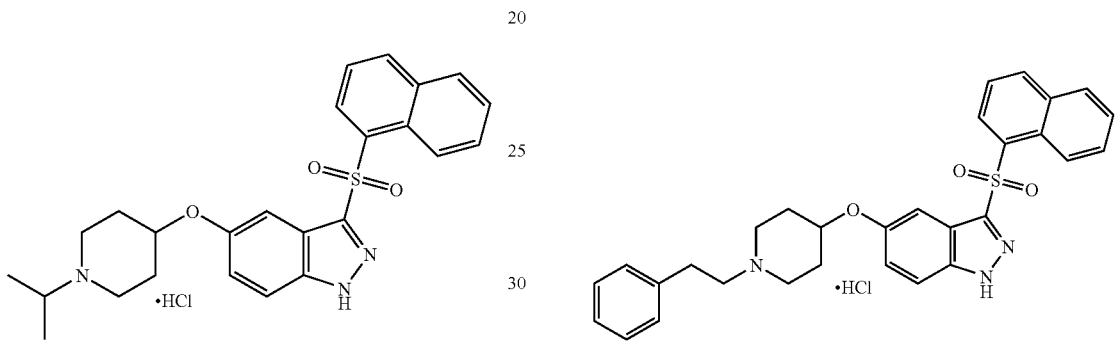

A suspension of 3-(1-naphthylsulfonyl)-5-(piperidin-4-yloxy)-1H-indazole (53.9 mg, 0.132 mmol) in 1,2-dichloroethane was treated sequentially with phenylacetaldehyde (0.17 mL, 1.5 mmol) and acetic acid (1.7 mL, 3.0 mmol), stirred at ambient temperature for 1.5 hours, treated with sodium triacetoxyborohydride (66.9 mg, 0.316 mmol), stirred at ambient temperature for 3-19 hours, diluted with chloroform and washed with 1.0 N sodium hydroxide and brine. (Methanol was added to the organic phase to aid in solubility.) The organic phase was dried over anhydrous magnesium sulfate and concentrated in vacuo. The resultant residue was purified by flash chromatography using 0.1-0.5% ammonium hydroxide/1.0-5.0% methanol in chloroform to yield 3-(1-naphthylsulfonyl)-5-{[1-(2-phenylethyl)piperidin-4-yl]oxy}-1H-indazole as an orange foam (45.8 mg, 67.8%). The foam was dissolved in methanol and chloroform, treated with isopropanolic HCl and concentrated in vacuo for 13 hours at 86° C. to give the title product as an orange foam (43.4 mg); Mass spectrum (+EI, [M+H]⁺) m/z 512. $^1$HNMR (500 MHz, DMSO-$d_6$): δ14.16 (d, 1H, J=4.52 Hz), 10.19-10.30 (m*, 1H), 8.70-8.76 (m, 1H), 8.56 (dd, 1H, J=7.32 Hz and 1.10 Hz), 8.27 (d, 1H, J=8.18 Hz), 8.04 (d, 1H, J=7.68 Hz), 7.70-7.75 (m, 1H), 7.55-7.63 (m, 3H), 7.10-7.39 (m*, 7H), 4.60-4.82 (m*, 1H), 3.60-3.65 (m, 1H), 3.38-3.45 (m, 1H), 3.30-3.36 (m*, 1H), 3.15-3.24 (m, 2H), 3.01-3.07 (m, 2H), 2.01-2.28 (m*, 3H), 1.80-1.95 ppm (m*, 1H). *Conformational isomers due to protonation of tertiary amine.

Example 24

Preparation of 5-[1-(Ethylpiperidin-4-yl)oxy]-3-(1-naphthylsulfonyl)-1H-indazole Hydrochloride

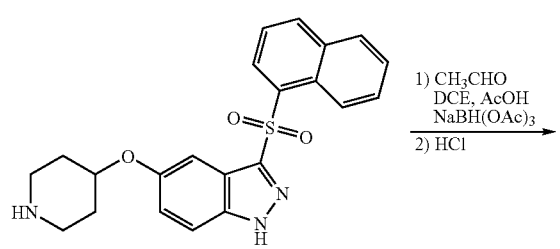

A suspension of 3-(1-naphthylsulfonyl)-5-(piperidin-4-yloxy)-1H-indazole (137 mg, 0.337 mmol) in 1,2-dichloroethane was treated sequentially with acetaldehyde (0.2 mL, 3.6 mmol) and acetic acid (0.2 mL, 3.5 mmol). The mixture was stirred under nitrogen at ambient temperature for 2.5-3 hours, treated with sodium triacetoxyborohydride (138 mg, 0.654 mmol), stirred for 3 hours at ambient temperatures, diluted with excess ethyl acetate and washed with 1.0 N or 2.5 N sodium hydroxide. The organic phase was washed with brine, dried over magnesium sulfate and concentrated in vacuo. The resultant residue was purified by flash chromatography with 0.5-1.0% ammonium hydroxide/5.0-10% methanol in chloroform and then by HPLC with 10-40% gradient of (20% methanol/chloroform) in hexane with 0.1% triethylamine to afford 5-[1-(ethylpiperidin-4-yl)oxy]-3-(1-naphthylsulfonyl)-1H-indazole as a light beige foam, 14.2 mg (9.66% yield). The foam was dissolved in methanol and chloroform, treated with isopropanolic HCl, stirred for 4.5 hours, concentrated and dried for 16 hours in vacuo at 84° C. to give the title product as a light yellow foam, 11.5 mg, Mass Spectrum (+EI, [M+H]$^+$) m/z 436. $^1$HNMR (500 MHz, DMSO-d$_6$): δ14.16 (s, 1H), 9.90-10.10 (br, s, 1H), 8.70-8.76 (m, 1H), 8.55 (d, 1H, J=7.32 Hz), 8.23-8.28 (m, 1H), 8.00-8.04 (m, 1H), 7.70-7.75 (m, 1H), 7.54-7.63 (m, 3H), 7.28-7.38 (m*, 1H), 7.09-7.20 (m*, 1H), 4.62-7.80 (m*, 1H), 3.31-3.53 (m*, 1H), 3.02-3.17 (m, 5H), 1.97-2.17 (m*, 3H), 1.79-1.86 (m, 1H), 1.16-1.42 ppm (m*, 3H). *Due to conformational isomers of HCl salt.

Example 25

Preparation of 5-[1-(Ethylpyrrolidin-3-yl)oxy]-3-(1-napthylsulfonyl)-1H-indazole Hydrochloride

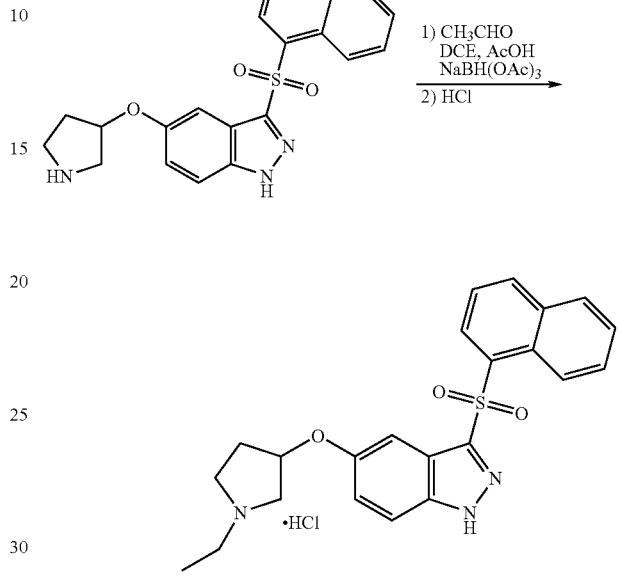

A solution of 3-(1-naphthylsulfonyl)-5-(pyrrolidin-3-yloxy)-1H-indazole (66.4 mg, 0.169 mmol) in methanol and chloroform was treated with isopropanolic HCl and concentrated in vacuo. The resultant residue was dispersed in 1,2-dichloroethane, treated sequentially with acetaldehyde (0.15 mL, 2.7 mmol) and acetic acid (0.15 mL, 2.6 mmol), stirred under nitrogen at ambient temperatures for 2 hours, treated with sodium triacetoxyborohydride (90.4 mg, 0.427 mmol), stirred for 91 hours at ambient temperatures, diluted with excess chloroform and washed with 1.0 N sodium hydroxide. The organic phase was washed with brine, dried over anhydrous magnesium sulfate and concentrated in vacuo. This residue was purified by flash chromatography with 0.5% N and then by HPLC with 10-40% gradient of (20% methanol/chloroform) in hexane with 0.1% triethylamine to yield 5-[1-(ethylpyrrolidin-3-yl)oxy]-3-(1-naphylsulfonyl)-1H-indazole as a light beige foam, 20.5 mg (28.8% yield). The foam was dispersed in methanol and chloroform, treated with isopropanolic HCl. stirred for 4.5 hours and concentrated for 16 hours in vacuo at 84° C. to afford the title product as a light beige foam, 18.3 mg, Mass Spectrum (+EI, [M+H]$^+$) m/z 422. $^1$HNMR (500 MHz, DMSO-d$_6$): δ14.21 (s, 1H), 10.33-10.80 (br, m*, 1H), 8.75 (d, 1H, J=8.54 Hz), 8.56 (d, 1H, J=7.08 Hz), 8.28 (d, 1H, J=8.30 Hz), 8.03-8.05 (m, 1H), 7.71-7.75 (m, 1H), 7.56-7.65 (m, 3H), 7.27 (s, 1H), 7.12 (dd, 1H, J=9.15 Hz and 2.32 Hz), 5.16-5.29 (m, 1H), 3.54-3.93 (m*, 2H), 3.11-3.47 (m*, 4H), 2.00-2.62 (m*, 2H), 1.20-1.23 ppm (m, 3H)*Due to conformational isomers of HCl salt.

Example 26

Preparation of 3-(1-Naphthylsulfonyl)-5-{[1-(2-phenylethyl)pyrrolidin-3-yl]oxy}-1H-indazole Hydrochloride

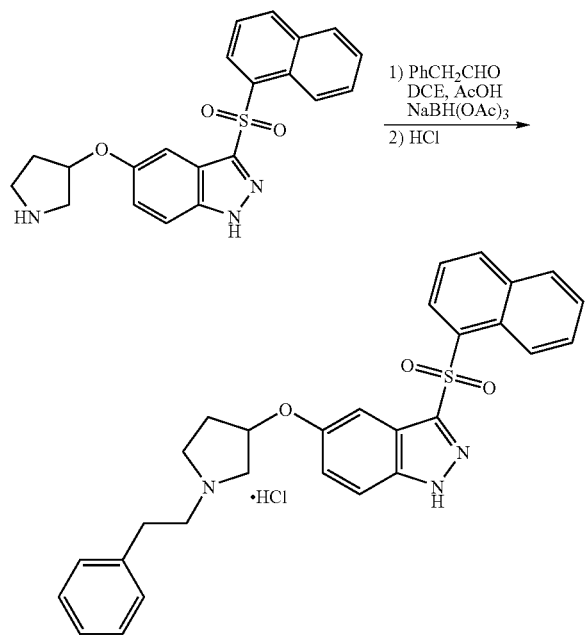

A suspension of 3-(1-naphthylsulfonyl)-5-(pyrrolidin-3-yloxy)-1H-indazole (51.8 mg, 0.132 mmol) in 1,2-dichloroethane was treated portionwise with phenacetaldehyde (0.2 mL, 0.2 mmol) and acetic acid (0.2 mL, 4 mmol), stirred for one hour at ambient temperature under nitrogen, treated with sodium triacetoxyborohydride (49.1 mg, 0.232 mmol), stirred for 2.5 hours, treated with sodium triacetoxyborohydride (37.5 mg, 0.177 mmol), stirred for 2.5 hours, poured into 1.0 N sodium hydroxide and extracted with chloroform. The extracts were combined, washed with brine, dried over anhydrous magnesium sulfate and concentrated in vacuo. The resultant residue was purified by flash chromatography using 100% chloroform and 0.05-0.2% ammonium hydroxide/0.5-2.0% methanol in chloroform to yield 3-(1-naphthylsulfonyl)-5-{[1-(2-phenylethyl)pyrrolidin-3-yl]oxy}-1H-indazole as a light yellow semi-solid, 24.6 mg (36.5% yield). The semi-solid was dissolved in methanol and chloroform, treated with isopropanolic HCl and concentrated in vacuo at 82° C. for 12 hours to give the title product as a brown foam, 24.6 mg, Mass spectrum (+ES, [M+H]$^+$) m/z 498. $^1$HNMR (500 MHz, DMSO-d$_6$): δ14.24 (d, 1H, J=4.88 Hz), 10.59-10.90 (m*, 1H), 8.77-8.79 (m, 1H), 8.59-8.60 (m, 1H), 8.31 (d, 1H, J=8.24 Hz), 8.07 (d, 1H, J=8.09 Hz), 7.75-7.78 (m, 1H), 7.60-7.68 (m, 3H), 7.24-7.37 (m, 6H), 7.15-7.19 (m, 1H), 5.25-5.31 (m*, 1H), 3.74-4.02 (m*, 2H), 3.31-3.55 (m*, 4H), 3.01-3.04 (m, 2H), 2.08-2.63 ppm (m*, 2H). *Conformational isomers due to protonation of tertiary amine.

Example 27

Preparation of 3-(1-naphthylsulfonyl)-5-(piperidin-4-ylmethoxy)-1H-indazole

Step 1:

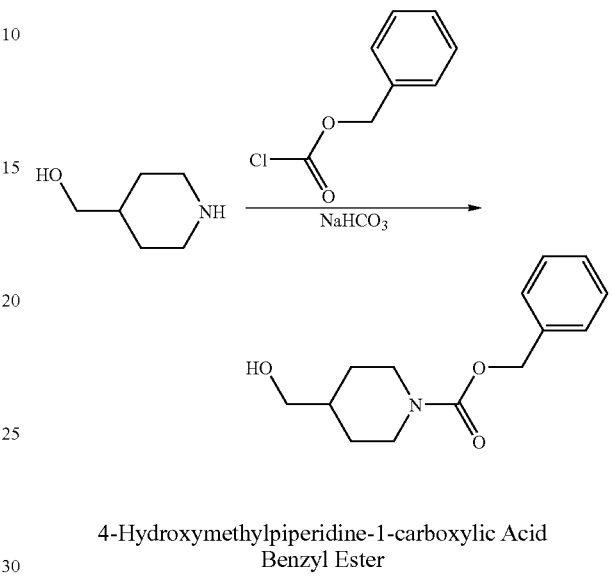

4-Hydroxymethylpiperidine-1-carboxylic Acid Benzyl Ester

A mixture of piperidin-4-yl-methanol (0.57 g, 5 mmoles), benzyl chloroformate (0.75 ml, 5.5 mmoles), and sodium bicarbonate (0.46 g, 5.5 mmoles) in CH$_2$Cl$_2$ was stirred at room temperature for 2 hours, diluted with H$_2$O and extracted with EtOAc. The extracts were combined, washed sequentially with water and brine, dried over Na$_2$SO$_4$ and concentrated under vacuum to afford the title compound (0.95 g, 3.8 mmoles).

Step 2:

4-[4-(Nitrophenoxy)methyl]piperidine-1-carboxylic Acid Benzyl Ester

A solution of 4-hydroxymethylpiperidine-1-carboxylic acid benzyl ester (0.7 g, 2.8 mmoles) in DMF was treated portionwise with NaH (0.1 g, 3.3 mmoles) at 0° C., allowed to warm to room temperature, treated with p-fluoronitrobenzene (0.34 ml, 3.3 mmoles), stirred at room temperature for 0.5 hour, diluted with H$_2$O and extracted with EtOAc. The extracts were combined, washed sequentially with water and brine, dried over Na$_2$SO$_4$ and concentrated under vacuum to afford the title compound (0.8 g, 2.16 mmoles).

Step 3:

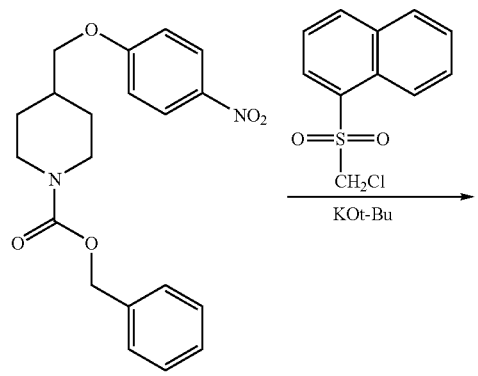

Step 4:

4-[3-(1-Naphthylsulfonylmethyl)-4-nitrophenoxymethyl]piperidine-1-carboxylic Acid Benzyl Ester A mixture of 4-(4-nitrophenoxymethyl)piperidine-1-carboxylic acid benzyl ester (0.8 g, 2.16 mmoles) and 1-chloromethanesulfonylnaphthalene (1.03 g, 4.3 mmoles) in THF (50 ml) at −78° C., under nitrogen, was treated dropwise with a solution of 1M potassium t-butoxide (6.5 ml, 6.5 mmoles) over a 30 minute period, allowed to warm to −40° C., stirred at −40° C. for 5 hours, poured into cold 2N HCl and extracted with EtOAc. The extracts were combined, dried over Na$_2$SO$_4$, and concentrated under vacuum. The resultant was purified by normal phase HPLC on a silica column, using as eluent 40% EtOAc/hexane, to afford the title compound as an off-white solid (0.9 g, 1.6 mmoles).

4-[4-Amino-3-(1-naphthylsulfonylmethyl)phenoxymethyl]piperidine-1-carboxylic Acid Benzyl Ester A mixture of 4-[3-(1-naphthylsulfonylmethyl)-4-nitrophenoxymethyl]-piperidine-1-carboxylic acid benzyl ester (0.9 g, 1.6 mmoles) and stannous chloride (1.8 g, 8 mmoles) in ethanol was heated at reflux temperature for 5 hours, cooled and concentrated under vacuum. The concentrate was diluted with water and extracted with EtOAc. The extracts were combined, dried over Na$_2$SO$_4$ and concentrated to afford the title compound (0.74 g, 1.36 mmoles).

Step 5:

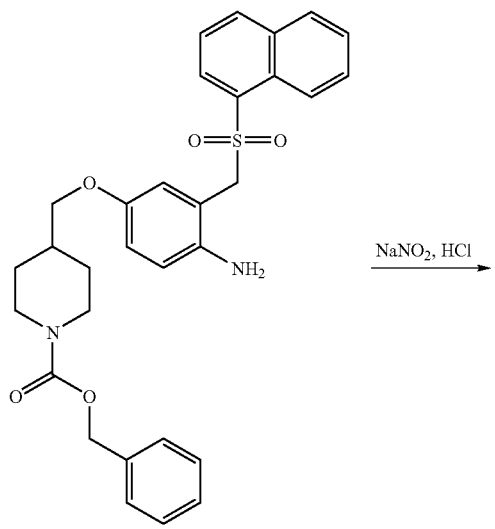

NaNO₂, HCl →

Step 6:

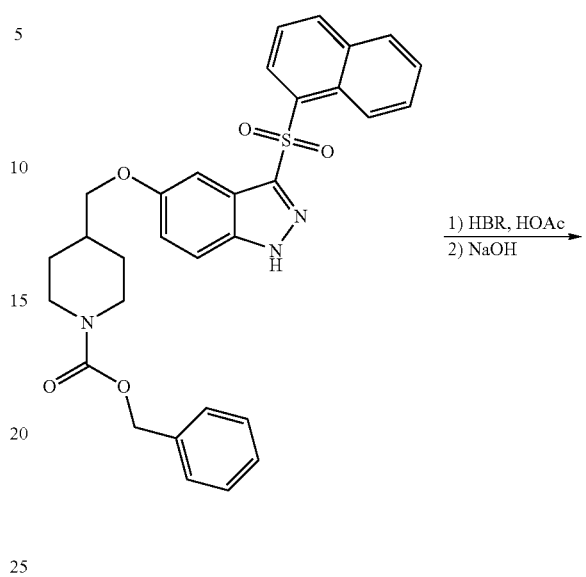

1) HBR, HOAc
2) NaOH →

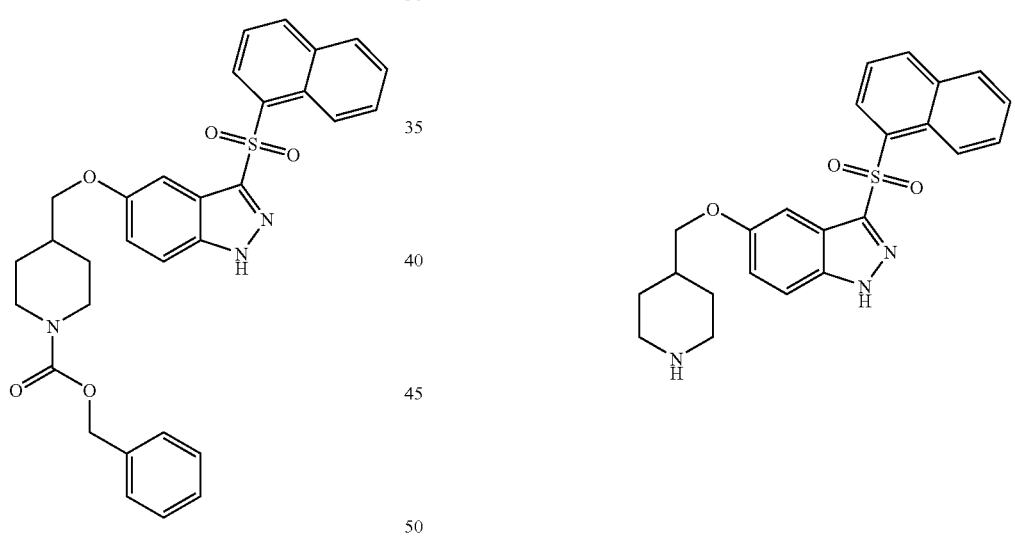

3-(1-Naphthylsulfonyl)-5-(piperidin-4-ylmethoxy)-1H-indazole

4-[3-(1-Naphthylsulfonyl)-1H-indazol-5-yloxymethyl]piperidine-1-carboxylic Acid Benzyl Ester A mixture of 4-[4-amino-3-(1-naphthylsulfonylmethyl)phenoxymethyl]-piperidine-1-carboxylic acid benzyl ester (0.74 g, 1.36 mmoles) in THF and 4M HCl (10 mL), under nitrogen, at 3° C. was treated dropwise with a solution of sodium nitrite (0.09 g, 1.42 mmoles) in H₂O, poured into a cold solution of saturated sodium bicarbonate and extracted with EtOAc. The extracts were combined, dried over Na₂SO₄ and concentrated under vacuum to afford the title compound as an off white solid (0.71 g, 1.29 mmoles).

A mixture of 4-[3-(1-naphthylsulfonyl)-1H-indazol-5-yloxymethyl]-piperidine-1-carboxylic acid benzyl ester (0.3 g, 0.54 mmoles) and 33 wt % HBr in acetic acid (1.5 mL) was stirred at room temperature for 30 minutes, diluted with ethyl ether and filtered. The filtercake was washed with ether, dried, treated with 1N NaOH and saturated NaCl and extracted with EtOAc. The extracts were combined, dried over Na₂SO₄ and concentrated under vacuum to afford the title compound as an off-white solid; mp 175-177° C., identified by HNMR and mass spectral analyses, MS (ES) m/z 420.2.

Example 28

Preparation of 3-(1-Naphthylsulfonyl)-5-(piperidin-3-ylmethoxy)-1H-indazole

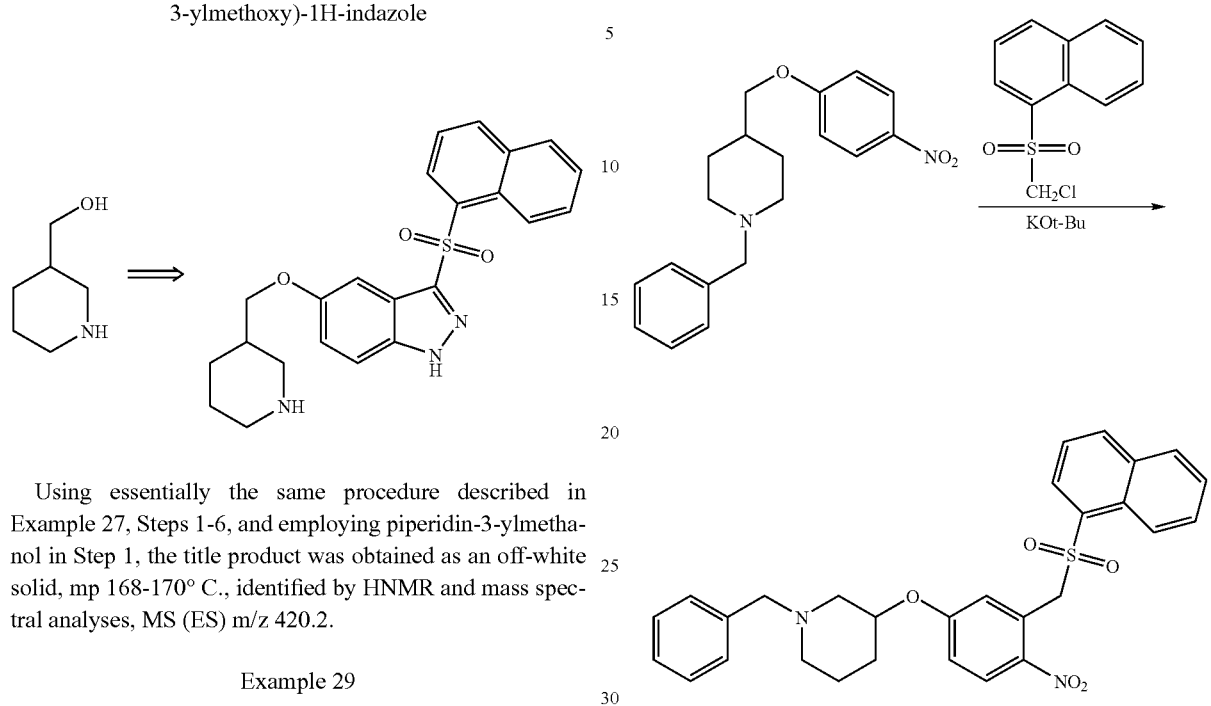

Using essentially the same procedure described in Example 27, Steps 1-6, and employing piperidin-3-ylmethanol in Step 1, the title product was obtained as an off-white solid, mp 168-170° C., identified by HNMR and mass spectral analyses, MS (ES) m/z 420.2.

Example 29

Preparation of 3-(1-Naphthylsulfonyl)-5-(piperidin-3-yloxy)-1H-indazole

Step 1

1-Benzyl-3-(4-nitrophenoxy)piperidine

A mixture of 1-benzyl-3-hydroxypiperidine (2.0 g, 10 mmoles), p-fluoro-nitrobenzene (1.06 ml, 12 mmoles) and sodium hydride (0.285 g, 12 mmoles) in DMF was stirred at room temperature for 3 hours, diluted with $H_2O$ and extracted with EtOAc. The extracts were combined, washed sequentially with water and brine, dried over $Na_2SO_4$ and concentrated under vacuum. The resultant residue was purified by flash chromatography using as eluent 50% EtOAc/hexane to afford the title compound (3.0 g, 9.43 mmoles).

Step 2:

1-Benzyl-3-[3-(1-Naphthylsulfonylmethyl)-4-nitrophenoxy]-piperidine

A mixture of 1-benzyl-3-(4-nitrophenoxy)piperidine (1.0 g, 3.14 mmoles) and 1-chloromethanesulfonylnaphthalene (0.9 g, 3.8 mmoles) in THF at −78° C. was treated dropwise with a solution of 1M potassium t-butoxide (9 mL, 9 mmoles) over a 30 minute period, warmed to −40° C., stirred at −40° C. for 5 hours, poured into cold 2N HCl and extracted with EtOAc. The extracts were combined, dried over $Na_2SO_4$ and concentrated under vacuum. The resultant residue was purified by normal phase HPLC on a silica column, using as eluent 40% EtOAc/hexane, to afford the title compound as an off-white solid (1.2 g, 2.3 mmoles).

Step 3:

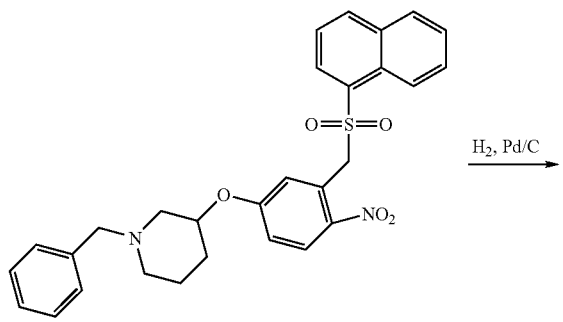

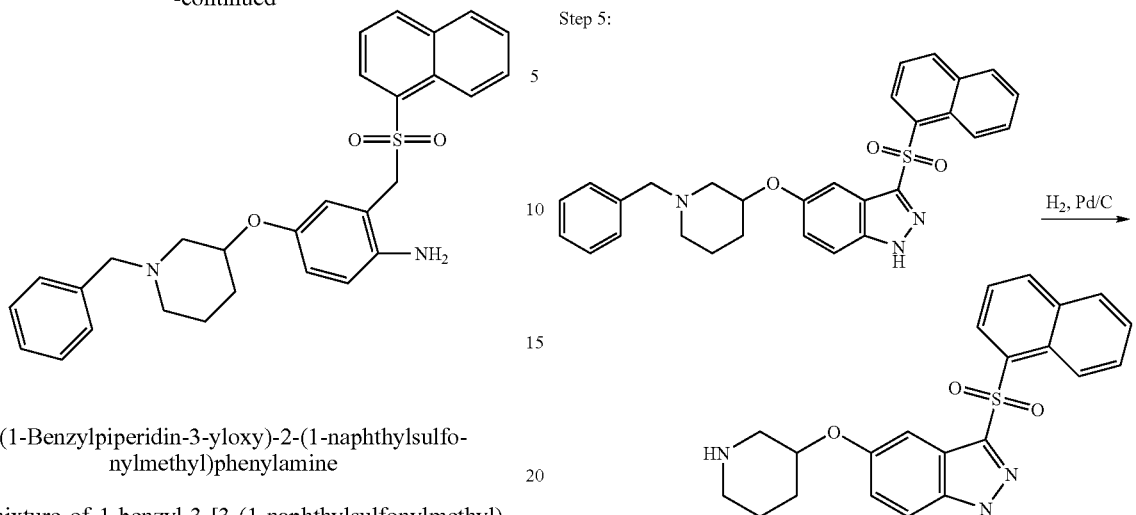

4-(1-Benzylpiperidin-3-yloxy)-2-(1-naphthylsulfonylmethyl)phenylamine

A mixture of 1-benzyl-3-[3-(1-naphthylsulfonylmethyl)-4-nitro-phenoxy]-piperidine (1.2 g, 2.3 mmoles) and 10% Pd/C in THF and methanol was hydrogenated in a Parr hydrogenation bottle at 52 lb/in² overnight. The reaction mixture was filtered through Celite, and the filtrate was concentrated under vacuum to afford the title compound as an off-white solid (1.0 g, 2.03 mmoles).

Step 4:

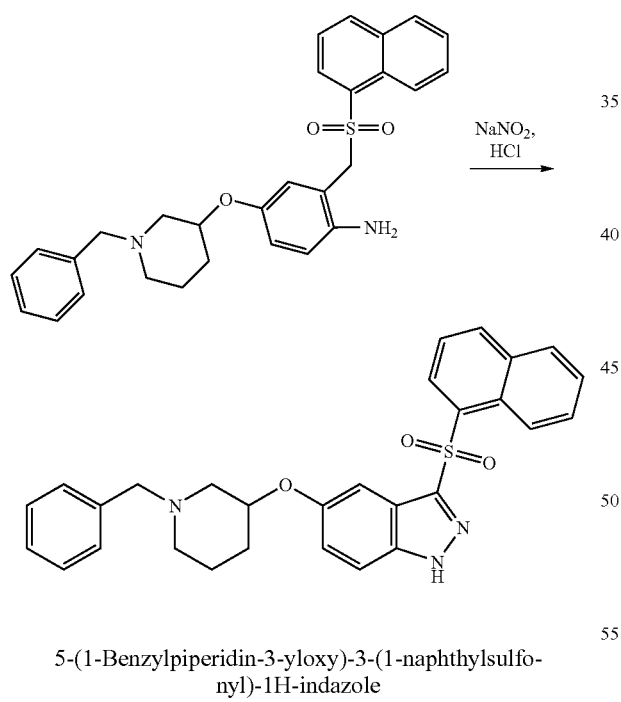

5-(1-Benzylpiperidin-3-yloxy)-3-(1-naphthylsulfonyl)-1H-indazole

A mixture of 4-(1-benzylpiperidin-3-yloxy)-2-(1-naphthylsulfonylmethyl)phenylamine (1.0 g, 2 mmoles) in THF and 4M HCl (10 mL), under nitrogen, at 3° C. was treated dropwise with a solution of sodium nitrite (0.16 g, 2.4 mmoles) in H₂O, poured into a cold solution of saturated sodium bicarbonate and extracted with EtOAc. The extracts were combined, dried over Na₂SO₄, and concentrated under vacuum to afford the title compound as an off white solid (0.7 g, 1.4 mmoles).

Step 5:

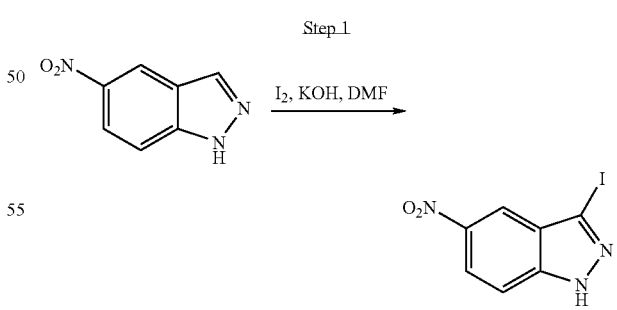

3-(1-Naphthylsulfonyl)-5-(piperidin-3-yloxy)-1H-indazole

A mixture of 5-(1-benzylpiperidin-3-yloxy)-3-(1-naphthylsulfonyl)-1H-indazole (0.7 g, 1.4 mmoles), 10% Pd/C and concentrated HCl (1 mL) in THF and methanol was hydrogenated in a Parr hydrogenation bottle at 52 lb/in² for 72 hours. TLC showed about 30% conversion into desired product. The reaction mixture was filtered through Celite, and the filtrate was concentrated. The concentrate, a mixture of starting material and product, was then separated by reverse phase chromatography on C18 column, using as eluent 10-100% H₂O/AcCN, to afford the title compound as an off-white solid, 0.16 g, mp 178-180° C., identified by HNMR and mass spectral analyses, MS (ES) m/z 406.1.

Example 30

Preparation of [3-(1-Naphthylsulfonyl)-1H-indazol-5-yl]-piperidin-4-ylamine Dihydrochloride Step 1

3-Iodo-5-nitro-1H-indazole

A solution of 5-nitroindazole (8.50 g, 52.13 mmol) in DMF was treated with iodine (26.46 g, 104.27 mmol) and potassium hydroxide pellets (11.70 g, 208.54 mmol) at room temperature, stirred for 4 days, poured into NaHSO₃ solution (11.06 g in 200 mL water) and filtered. The filtercake was washed with water and dried in vacuo to provide the title compound as a yellow solid, 14.74 g (98% yield), characterized by NMR and mass spectral analyses.

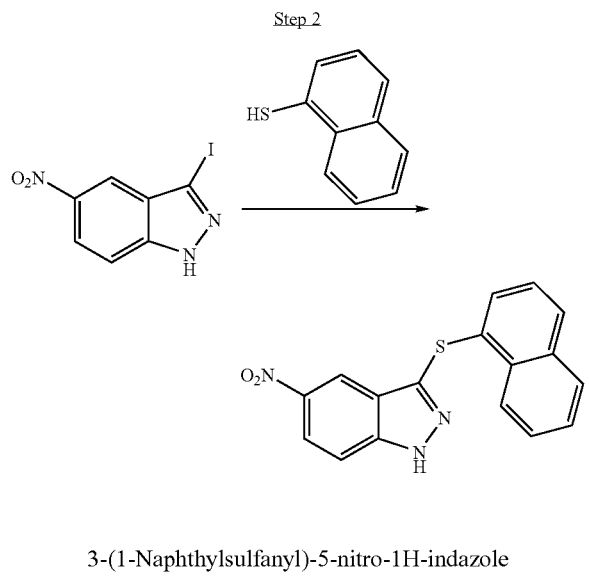

3-(1-Naphthylsulfanyl)-5-nitro-1H-indazole

A mixture of 3-iodo-5-nitro-1H-indazole (10.00 g, 34.60 mmol), 1-naphthylthiol (5.54 g, 34.60 mmol), CuI (0.659 g, 3.46 mmol) and ethylene glycol (4.30 g, 69.20 mmol) in isopropanol was heated at 90° C. under nitrogen overnight, cooled, diluted with 30% MeOH in CH₂Cl₂, and filtered through a pad of silica gel. The filtrate was concentrated in vacuo. The concentrate was purified by chromatography with 1% MeOH in CH₂Cl₂ to provide the title compound, 5.5 g (49% yield), characterized by NMR and mass spectral analyses.

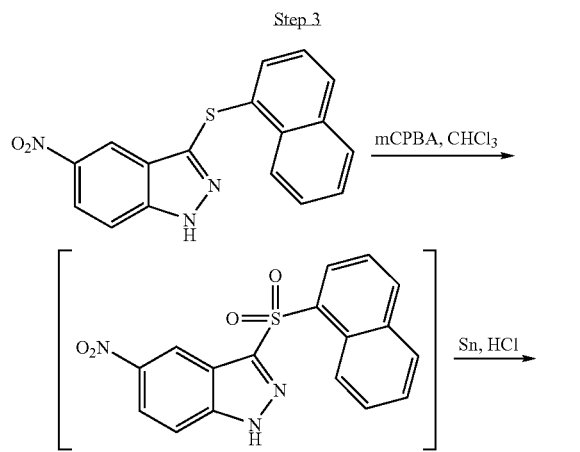

[3-(1-Naphthylsulfonyl)-1H-indazol-5-yl]amine

A mixture of 3-(1-naphthylsulfanyl)-5-nitro-1H-indazole (5.50 g, 17.11 mmol) and 3-chloroperoxybenzoic acid (17.91 g, 103.80 mmol) in CHCl₃ was stirred at room temperature for 4 hours, diluted with EtOAc, washed sequentially with Na₂SO₃ solution, water and brine, dried over Na₂SO₄, and concentrated in vacuo to give a residue. A mixture of this residue, tin mossy (15.79 g, 133.01 mmol) in MeOH and conc. hydrochloric acid was heated at 60° C., cooled to room temperature, diluted with CH₂Cl₂ and basified with NaOH. The phases were separated. The aqueous phase was extracted with CH₂Cl₂. The organic phase and the extracts were combined, dried over Na₂SO₄ and concentrated in vacuo. The resultant residue was purified chromatographically, to provide the title compound, 2.50 g, (45% overall yield), characterized by HNMR and mass spectral analyses. MS (ES⁺) m/e 324 (MH⁺).

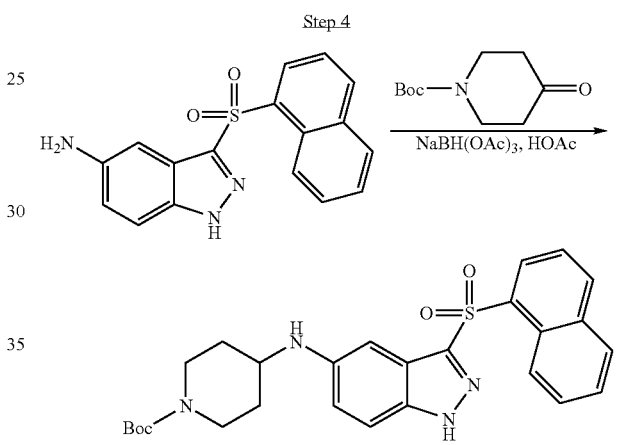

4-{[3-(1-Naphthylsulfonyl)-1H-indazol-5-yl]amino}piperidine-1-carboxylic Acid Tert-butyl Ester A mixture of [3-(1-naphthylsulfonyl)-1H-indazol-5-yl]amine (400 mg, 1.24 mmol), 1-Boc-4-piperidone (493 mg, 2.47 mmol), sodium triacetoxyborohydride (524 mg, 2.47 mmol), and acetic acid (149 mg, 2.47 mmol) in 1,2-dichloroethane was stirred at room temperature overnight, diluted with CH₂Cl₂, washed with water, dried over Na₂SO₄ and concentrated in vacuo. The resultant residue was purified by column chromatography with 1% MeOH in CH₂Cl₂ as eluent to provide the title compound, 390 mg (62% yield), characterized by HNMR and mass spectral analyses.

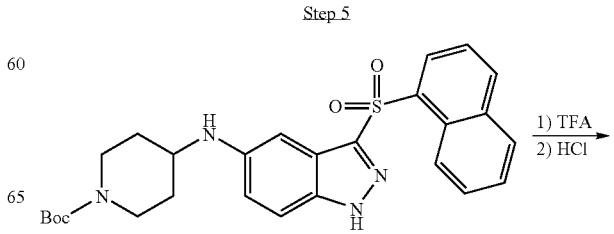

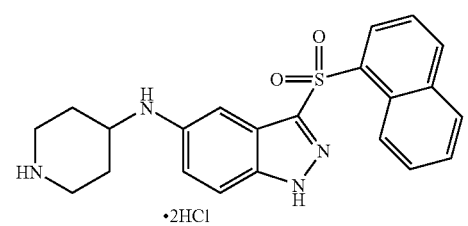

[3-(1-Naphthylsulfonyl)-1H-indazol-5-yl]piperidin-4-ylamine Dihydrochloride

A solution of {4-[3-(1-naphthylsulfonyl)-1H-indazol-5-yl]amino}piperidine-1-carboxylic acid tert-butyl ester (390 mg, 0.77 mmol) 1:1 TFA/CH$_2$Cl$_2$ (v/v) was stirred at room temperature for 2 hours and concentrated to dryness in vacuo. The resultant residue was dispersed in methanol and chloroform, treated with ethereal HCl and concentrated in vacuo to afford the title compound, 359 mg (98% yield), characterized by HNMR and mass spectral analyses, MS (ES$^+$) m/e 407 (MH$^+$).

Example 31

Preparation of 3-(1-Naphthylsulfonyl)-N-(piperidin-4-ylmethyl)-1H-indazol-5-amine Dihydrochloride

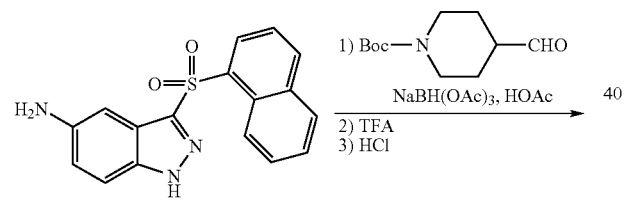

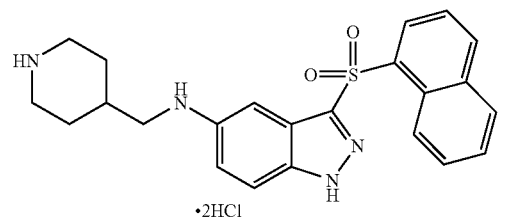

Using essentially the same procedure described in Example 30 and employing 1-Boc-piperidin-4-ylcarboxaldehyde, the title compound was obtained as a yellow solid, identified by HNMR and mass spectral analyses, MS (ES$^+$) m/e 421 (MH$^+$).

Example 32

Preparation of 3-(1-Naphthylsulfonyl)-N-piperidin-3-yl-1H-indazol-5-amine Dihydrochloride

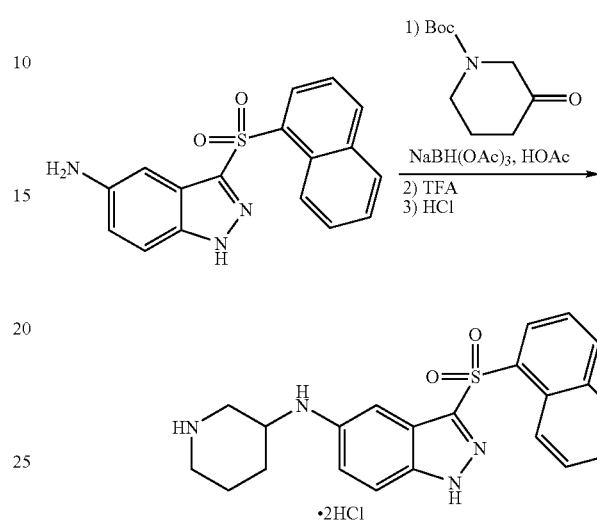

Using essentially the same procedure described in Example 30 and employing 1-Boc-3-piperidone, the title product was obtained as a light brown solid, identified by HNMR and mass spectral analyses, MS (ES$^+$) m/e 421 (MH$^+$).

Example 33

Preparation of 3-(1-Naphthylsulfonyl)-N-piperidin-4-yl-1H-indazol-6-amine Dihydrochloride

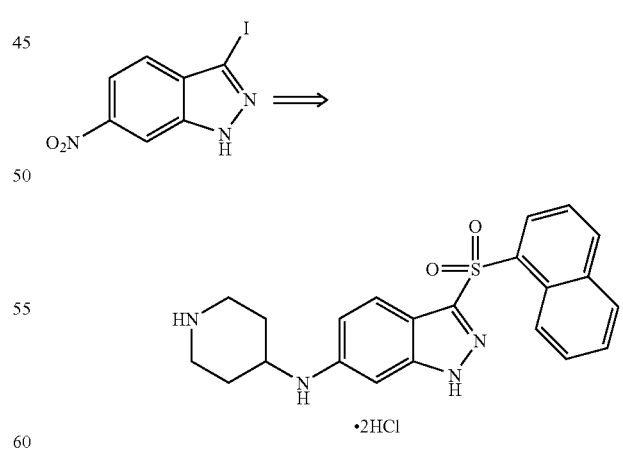

Using essentially the same procedure described in Example 30 and employing 3-iodo-6-nitro-1H-indazole in Step 2, the title product was obtained as a light brown solid, identified by HNMR and mass spectral analyses, MS (ES$^+$) m/e 407 (MH$^+$).

Example 34

Preparation of 3-(1-Naphthylsulfonyl)-N-piperidin-3-yl-1H-indazol-6-amine Dihydrochloride

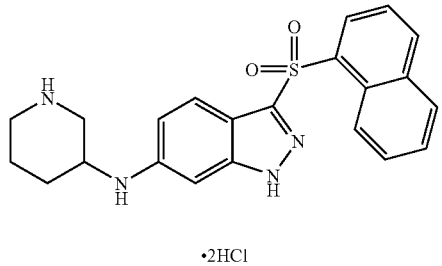

•2HCl

Using essentially the same procedure described in Example 30 and employing 6-nitro-1H-indazole in Step 1 and 1-Boc-3-piperidone in Step 4, the title product was obtained as an orange solid, identified by HNMR and mass spectral analyses, MS (ES$^+$) m/e 407 (MH$^+$).

Example 35

Preparation of 3-(1-Naphthylsulfonyl)-N-(piperidin-4-ylmethyl)-1H-indazol-6-amine Dihydrochloride

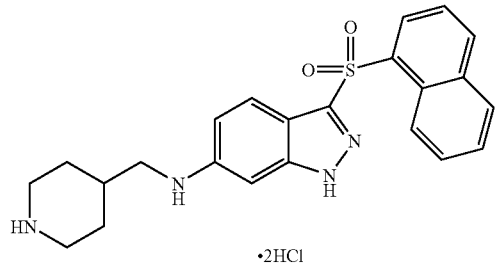

•2HCl

Using essentially the same procedure described in Example 30 and employing 6-nitro-1H-indazole in Step 1 and 1-Boc-piperidin-4-ylcarboxaldehyde in Step 4, the title product was obtained as a brown solid, identified by HNMR and mass spectral analyses, MS (ES$^+$) m/e 407 (MH$^+$).

Example 36

Preparation of 3-(1-Naphthylsulfonyl)-N-piperidin-4-yl-1H-indazol-7-amine Dihydrochloride

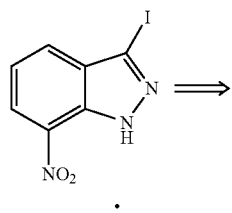

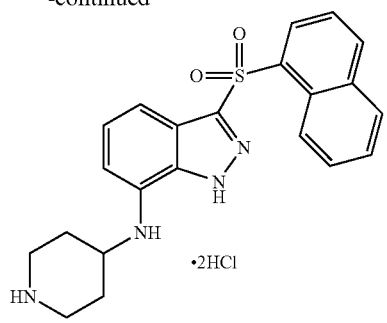

•2HCl

Using essentially the same procedure described in Example 30 and employing 7-nitro-1H-indazole in Step 2, the title compound was obtained as an off-white solid, identified by HNMR and mass spectral analyses, MS (ES$^+$) m/e 407 (MH$^+$).

Example 37

Preparation of 3-(1-Naphthylsulfonyl)-N-piperidin-3-yl-1H-indazol-7-amine Dihydrochloride

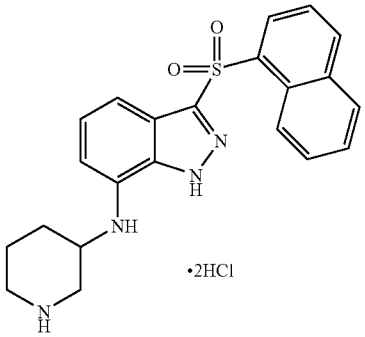

•2HCl

Using essentially the same procedure described in Example 30 and employing 7-nitro-1H-indazole in Step 1 and 1-Boc-3-piperidone in Step 4, the title compound was obtained as a dark brown solid, identified by HNMR and mass spectral analyses, MS (ES$^+$) m/e 435 (MH$^+$).

Example 38

Preparation of 3-(1-Naphthylsulfonyl)-N-(piperidin-4-ylmethyl)-1H-indazol-7-amine Dihydrochloride

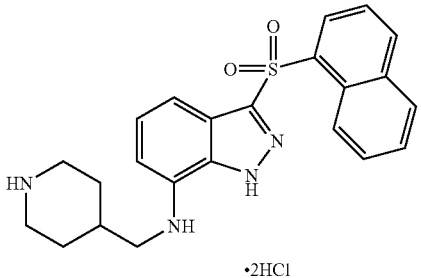

•2HCl

Using essentially the same procedure described in Example 30 and employing 7-nitro-1H-indazole in Step 1 and 1-Boc-piperidin-4-ylcarboxaldehyde in Step 4, the title compound was obtained as a dark brown solid, identified by HNMR and mass spectral analyses MS (ES$^+$) m/e 435 (MH$^+$).

Example 39

Preparation of 3-(1-Naphthylsulfonyl)-N-piperidin-4-yl-1H-indazol-4-amine Dihydrochloride

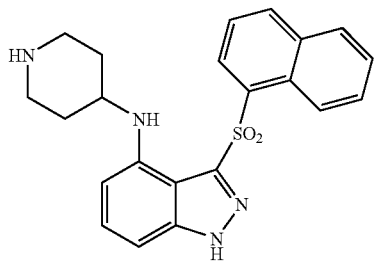

•2HCl

Using essentially the same procedure described in Example 30 and employing 4-nitro-1-H-indazole in Step 1, the title compound was obtained as a yellow solid, identified by HNMR and mass spectral analyses, MS (ES+) m/e 407 (MH+).

Example 40

Preparation of 3-(1-Naphthylsulfonyl)-N-piperidin-3-yl-1H-indazol-4-amine Dihydrochloride

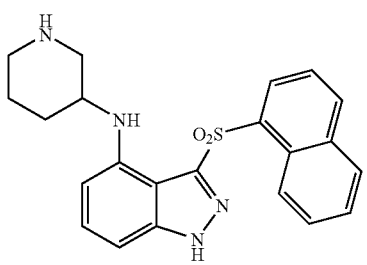

•2HCl

Using essentially the same procedure described in Example 30 and employing 4-nitro-1-H-indazole in Step 1 and 1-Boc-3-piperidone in Step 4, the title compound was obtained as a dark green solid, identified by HNMR and mass spectral analyses, MS (ES+) m/e 407 (MH+).

Example 41

Preparation of 3-(1-Naphthylsulfonyl)-N-(piperidin-4-ylmethyl)-1H-indazol-4-amine Dihydrochloride

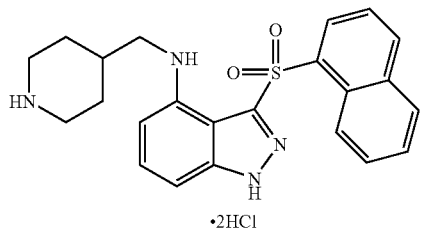

•2HCl

Using essentially the same procedure described in Example 30 and employing 4-nitro-1-H-indazole in Step 1 and 1-Boc-piperidin-4-ylcarboxaldehyde in Step 4, the title compound was obtained as a green solid, identified by HNMR and mass spectral analyses, MS (ES+) m/e 421 (MH+).

Examples 42-51

Preparation of 3-Arylsulfonyl N-piperidin-4-yl-1H-indazol-5-amine Dihydrochloride Compounds

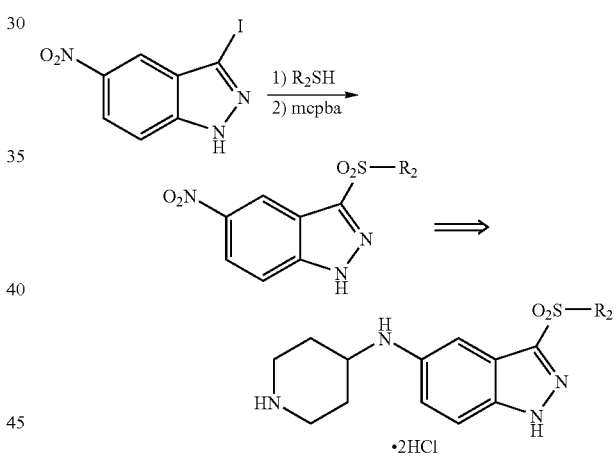

Using essentially the same procedure described in Example 30 and employing the desired arylthiol in Step 2, the compounds shown in Table II were obtained and identified by HNMR and mass spectral analyses.

TABLE II

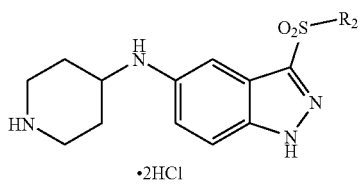

•2HCl

| Example No. | R2 | [M + H] |
|---|---|---|
| 42 | 3-chlorophenyl | 391 |
| 43 | 4-chlorophenyl | 391 |

TABLE II-continued

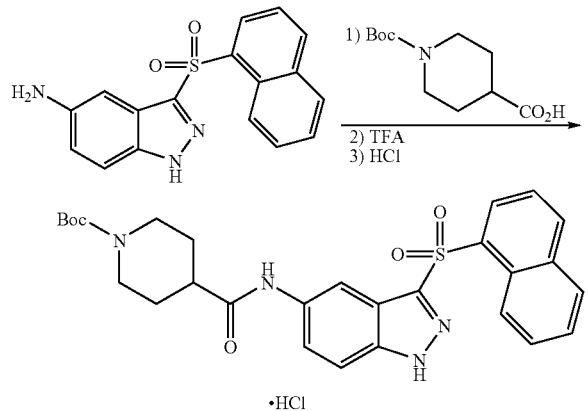

| Example No. | R2 | [M + H] |
|---|---|---|
| 44 | 2-naphthyl | 407 |
| 45 | 3-fluorophenyl | 375 |
| 46 | 4-fluorophenyl | 375 |
| 47 | 4-isopropylphenyl | 399 |
| 48 | 4-(trifluoromethyl)phenyl | 425 |
| 49 | phenyl | 357 |
| 50 | 4-methoxyphenyl | 387 |
| 51 | 3-methylphenyl | 371 |

Example 52

Preparation of N-[3-(1-Naphthylsulfonyl)-1H-indazol-5-yl]piperidine-4-carboxamide Hydrochloride

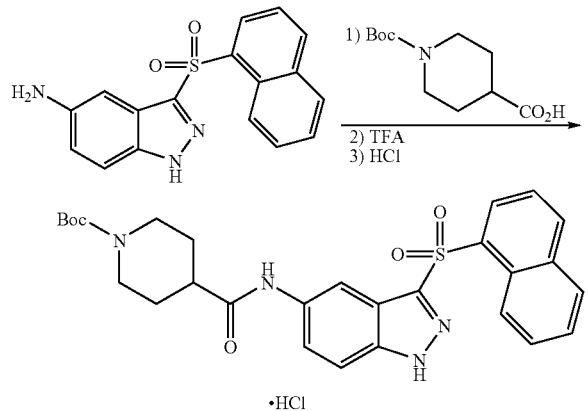

A mixture of 3-(1-naphthylsulfonyl)-1H-indazol-5-amine (300 mg, 0.928 mmol), 1-Boc-piperidine-4-carboxylic acid (276 mg, 1.21 mmol), 1-[3-(dimethylamino)propyl)]-3-ethylcarbodiimide hydrochloride (231 mg, 1.21 mmol) in CH$_3$CN was stirred at room temperature overnight and concentrated to dryness to provide a residue. The residue was treated with TFA at room temperature for 2 hours and concentrated to dryness in vacuo. The resultant residue was purified by reverse phase HPLC to give a solid. The solid was dispersed in methanol and chloroform, treated with aqueous HCl solution, concentrated and dried in vacuo to provide the title compound as a milky light orange solid, characterized by HNMR and mass spectral analyses, MS (ES$^+$) m/e 435 (MH$^+$).

Example 53

N-[3-(1-Naphthylsulfonyl)-1H-indazol-6-yl]piperidine-4-carboxamide Dihydrochloride

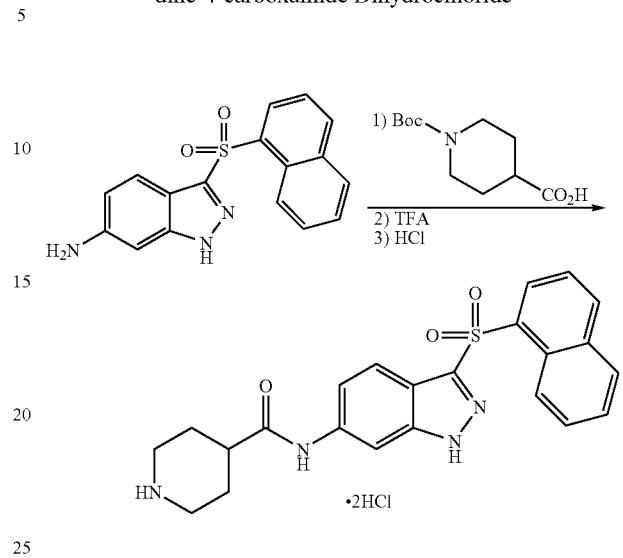

Using essentially the same procedure described in Example 52 and employing [3-(1-naphthylsulfonyl)-1H-indazol-6-amine, the title product was obtained as a light brown solid, identified by HNMR and mass spectral analyses, MS (ES$^+$) m/e 435 (MH$^+$).

Example 54

N-[3-(1-Naphthylsulfonyl)-1H-indazol-7-yl]piperidine-4-carboxamide Dihydrochloride

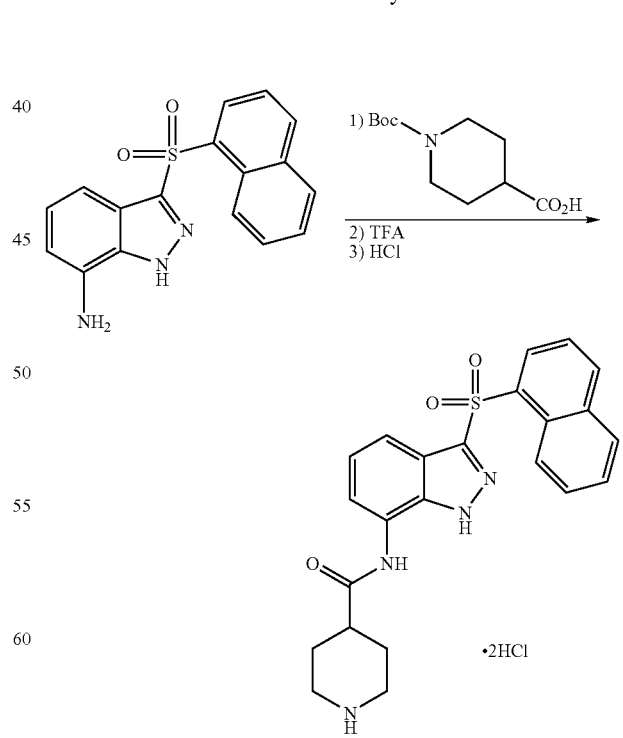

Using essentially the same procedure described in Example 52 and employing [3-(1-naphthylsulfonyl)-1H-indazol-7-amine, the title product was obtained as a brown gum, identified by HNMR and mass spectral analyses, MS (ES⁺) m/e 435 (MH⁺).

Example 55

N-[3-(1-Naphthylsulfonyl)-1H-indazol-7-yl]piperidine-3-carboxamide Dihydrochloride

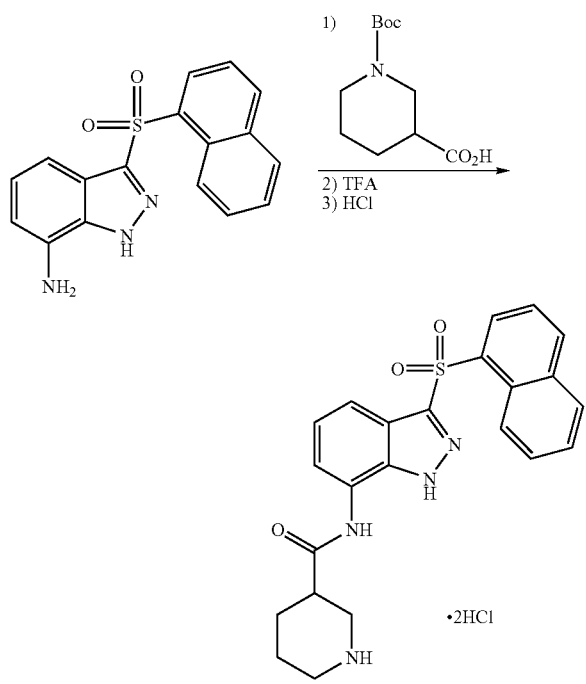

Using essentially the same procedure described in Example 52 and employing [3-(1-naphthylsulfonyl)-1H-indazol-7-amine and 1-Boc-piperidine-3-carboxylic acid, the title product was obtained as a brown solid, identified by HNMR and mass spectral analyses, MS (ES⁺) m/e 435 (MH⁺).

Example 56

Evaluation of 5-HT$_6$ Binding Affinity of Test Compounds

The affinity of test compounds for the serotonin 5-HT$_6$ receptor was evaluated in the following manner. Cultured Hela cells expressing human cloned 5-HT$_6$ receptors were harvested and centrifuged at low speed (1,000×g) for 10.0 minutes to remove the culture media. The harvested cells were suspended in half volume of fresh physiological phosphate buffered saline solution and recentrifuged at the same speed. This operation was repeated. The collected cells were then homogenized in ten volumes of 50 mM Tris.HCl (pH 7.4) and 0.5 mM EDTA. The homogenate was centrifuged at 40,000×g for 30.0 min and the precipitate was collected. The obtained pellet was resuspended in 10 volumes of Tris.HCl buffer and recentrifuged at the same speed. The final pellet was suspended in a small volume of Tris.HCl buffer and the tissue protein content was determined in aliquots of 10-25 µl volumes. Bovine Serum Albumin was used as the standard in the protein determination according to the method described in Lowry et al., *J. Biol. Chem.*, 193: 265 (1951). The volume of the suspended cell membranes was adjusted to give a tissue protein concentration of 1.0 mg/ml of suspension. The prepared membrane suspension (10 times concentrated) was aliquoted in 1.0 ml volumes and stored at −70° C. until used in subsequent binding experiments.

Binding experiments were performed in a 96 well microtiter plate format, in a total volume of 200 µl. To each well was added the following mixture: 80.0 µl of incubation buffer made in 50 mM Tris.HCl buffer (pH 7.4) containing 10.0 mM MgCl$_2$ and 0.5 mM EDTA and 20 µl of [³H]-LSD (S.A., 86.0 Ci/mmol, available from Amersham Life Science), 3.0 nM. The dissociation constant, K$_D$ of the [³H]LSD at the human serotonin 5-HT$_6$ receptor was 2.9 nM, as determined by saturation binding with increasing concentrations of [³H]LSD. The reaction was initiated by the final addition of 100.0 µl of tissue suspension. Nonspecific binding was measured in the presence of 10.0 µM methiothepin. The test compounds were added in 20.0 µl volume.

The reaction was allowed to proceed in the dark for 120 minutes at room temperature, at which time, the bound ligand-receptor complex was filtered off on a 96 well unifilter with a Packard Filtermate® 196 Harvester. The bound complex caught on the filter disk was allowed to air dry and the radioactivity is measured in a Packard TopCount® equipped with six photomultiplier detectors, after the addition of 40.0 µl Microscint®-20 scintillant to each shallow well. The unifilter plate was heat-sealed and counted in a PackardTopCount® with a tritium efficiency of 31.0%.

Specific binding to the 5-HT$_6$ receptor was defined as the total radioactivity bound less the amount bound in the presence of 10.0 µM unlabeled methiothepin. Binding in the presence of varying concentrations of test compound was expressed as a percentage of specific binding in the absence of test compound. The results were plotted as log % bound versus log concentration of test compound. Nonlinear regression analysis of data points with a computer assisted program Prism® yielded both the IC$_{50}$ and the K$_i$ values of test compounds with 95% confidence limits. A linear regression line of data points was plotted, from which the IC$_{50}$ value is determined and the K$_i$ value is determined based upon the following equation:

$$K_i = IC_{50}/(1+L/K_D)$$

where L was the concentration of the radioactive ligand used and K$_D$ is the dissociation constant of the ligand for the receptor, both expressed in nM.

Using this assay, the following Ki values were determined. The data are shown in Table III, below.

TABLE III

For Table III
A = 0.01 nM-10 nM
B = 11 nM-25 nM
C = 26 nM-35 nM
D = 36 nM-45 nM
E = >45 nM TABLE III-continued

| Test Compound (Example No.) | 5-HT$_6$ Binding Ki (nM) |
|---|---|
| 1 | A |
| 2 | A |
| 3 | A |
| 4 | A |
| 5 | A |
| 6 | A |
| 7 | B |
| 8 | B |
| 9 | E |
| 10 | A |
| 11 | B |
| 12 | A |
| 13 | A |
| 14 | E |
| 15 | A |
| 16 | B |
| 17 | B |
| 18 | A |
| 19 | A |
| 20 | A |
| 21 | A |
| 22 | A |
| 23 | B |
| 24 | A |
| 25 | A |
| 26 | B |
| 27 | B |
| 28 | A |
| 29 | A |
| 30 | A |
| 31 | A |
| 32 | A |
| 33 | E |
| 34 | E |
| 35 | D |
| 36 | C |
| 37 | E |
| 38 | B |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | C |
| 54 | C |
| 55 | A |

What is claimed is:

1. A compound of formula I

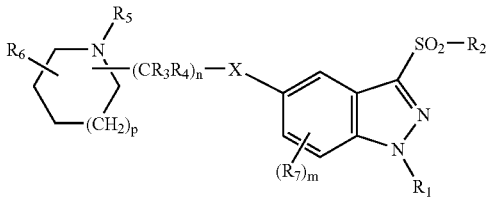

wherein
X is O, S, NR, CH$_2$, CO, CH$_2$O, CH$_2$S, CH$_2$NR, CH$_2$CO, CONR or NRCO;

n is 0 or an integer of 1, 2, 3, 4, 5, or 6;
R is H or an optionally substituted alkyl group;
R$_1$ is H or an alkyl, cycloalkyl, aryl or heteroaryl group each optionally substituted;
R$_2$ is an optionally substituted alkyl, cycloalkyl, aryl or heteroaryl group or an optionally substituted 8- to 13-membered bicyclic or tricyclic ring system having a N atom at the bridgehead and optionally containing 1, 2 or 3 additional heteroatoms selected from N, O or S;
R$_3$ and R$_4$ are each independently H, or an optionally substituted alkyl group;
R$_5$ is H, COR$_{12}$ or an alkyl, alkenyl, alkynyl, cycloalkyl, cycloheteroalkyl, aryl or heteroaryl group each optionally substituted;
R$_6$ is H or an optionally substituted alkyl group;
p is the integer 1;
R$_7$ is H, halogen, CN, OR$_8$, CO$_2$R$_9$, CONR$_{10}$R$_{11}$, or an alkyl, alkenyl, alkynyl, cycloalkyl, cycloheteroalkyl, aryl or heteroaryl group each optionally substituted;
m is an integer of 1, 2 or 3;
R$_8$ is H, COR$_{12}$ or an alkyl, alkenyl, alkynyl, aryl or heteroaryl group each optionally substituted;
R$_9$ is H or a C$_1$-C$_6$alkyl, aryl or heteroaryl group each optionally substituted;
R$_{10}$ and R$_{11}$ are each independently H or an optionally substituted alkyl group; and
R$_{12}$ is an optionally substituted C$_1$-C$_6$alkyl, cycloalkyl, cycloheteroalkyl, aryl or heteroaryl group; or
a stereoisomer thereof or a pharmaceutically acceptable salt thereof.

2. The compound according to claim 1 wherein X is O, NR or CH$_2$.

3. The compound according to claim 1 wherein n is 0 or 1.

4. The compound according to claim 2 wherein R$_2$ is an optionally substituted aryl or heteroaryl group or an optionally substituted 8- to 13-membered bicyclic or tricyclic ring system having a N atom at the bridgehead and optionally containing 1, 2 or 3 additional heteroatoms selected from N, O or S.

5. The compound according to claim 3 wherein X is O or NH.

6. The compound according to claim 5 wherein R$_5$ is H or C$_1$-C$_4$alkyl.

7. The compound according to claim 5 wherein R$_2$ is an optionally substituted naphthyl or imidazothiazolyl group.

8. The compound according to claim 1 selected from the group consisting of:
3-(1-naphthylsulfonyl)-5-(piperidin-4-yloxy)-1H-indazole;
3-(1-naphthylsulfonyl)-5-[(1-propylpiperidin-4-yl)oxy]-1H-indazole;
5-[(1-butylpiperidin-4-yl)oxy]-3-(1-naphthylsulfonyl)-1H-indazole;
5-[(1-methylpiperidin-4-yl)oxy]-3-(1-naphthylsulfonyl)-1H-indazole;
5-[(1-isopropylpiperidin-4-yl)oxy]-3-(1-naphthylsulfonyl)-1H-indazole;
3-(1-naphthylsulfonyl)-5-{[1-(2-phenylethyl)piperidin-4-yl]oxy}-1H-indazole;
5-[(1-ethylpiperidin-4-yl)oxy]-3-(1-naphthylsulfonyl)-1H-indazole;
3-(1-naphthylsulfonyl)-5-(piperidin-4-ylmethoxy)-1H-indazole;
3-(1-naphthylsulfonyl)-5-(piperidin-3-ylmethoxy)-1H-indazole;
3-(1-naphthylsulfonyl)-5-(piperidin-3-yloxy)-1H-indazole;

3-(1-naphthylsulfonyl)-N-piperidin-4-yl-1H-indazol-5-amine;
3-(1-naphthylsulfonyl)-N-(piperidin-4-ylmethyl)-1H-indazol-5-amine;
3-(1-naphthylsulfonyl)-N-piperidin-3-yl-1H-indazol-5-amine;
N-[3-(1-naphthylsulfonyl)-1H-indazol-5-yl]piperidine-4-carboxamide;
3-(phenylsulfonyl)-5-(piperidin-4-yloxy)-1H-indazole;
3-[(3-fluorophenyl)sulfonyl]-5-(piperidin-4-yloxy)-1H-indazole;
3-[(2-chlorophenyl)sulfonyl]-5-(piperidin-4-yloxy)-1H-indazole;
3-[(3-chlorophenyl)sulfonyl]-5-(piperidin-4-yloxy)-1H-indazole;
3-[(4-chlorophenyl)sulfonyl]-5-(piperidin-4-yloxy)-1H-indazole;
3-[(3-methylphenyl)sulfonyl]-5-(piperidin-4-yloxy)-1H-indazole;
3-[(3-methoxyphenyl)sulfonyl]-5-(piperidin-4-yloxy)-1H-indazole;
3-[(4-methoxyphenyl)sulfonyl]-5-(piperidin-4-yloxy)-1H-indazole;
5-(piperidin-4-yloxy)-3-{[3-(trifluoromethyl)phenyl]sulfonyl}-1H-indazole;
5-(piperidin-4-yloxy)-3-{[4-(trifluoromethyl)phenyl]sulfonyl}-1H-indazole;
3-[(4-isopropylphenyl)sulfonyl]-5-(piperidin-4-yloxy)-1H-indazole;
3-[(4-methyl-1-naphthyl)sulfonyl]-5-(piperidin-4-yloxy)-1H-indazole;
3-[(3-chlorophenyl)sulfonyl]-N-piperidin-4-yl-1H-indazol-5-amine;
3-[(4-chlorophenyl)sulfonyl]-N-piperidin-4-yl-1H-indazol-5-amine;
3-(2-naphthylsulfonyl)-N-piperidin-4-yl-1H-indazol-5-amine;
3-[(3-fluorophenyl)sulfonyl]-N-piperidin-4-yl-1H-indazol-5-amine;
3-[(4-fluorophenyl)sulfonyl]-N-piperidin-4-yl-1H-indazol-5-amine;
3-[(4-isopropylphenyl)sulfonyl]-N-piperidin-4-yl-1H-indazol-5-amine;
N-piperidin-4-yl-3-{[4-(trifluoromethyl)phenyl]sulfonyl}-1H-indazol-5-amine;
3-(phenylsulfonyl)-N-piperidin-4-yl-1H-indazol-5-amine;
3-[(4-methoxyphenyl)sulfonyl]-N-piperidin-4-yl-1H-indazol-5-amine; and
3-[(3-methylphenyl)sulfonyl]-N-piperidin-4-yl-1H-indazol-5-amine; or
a stereoisomer thereof; or
a pharmaceutically acceptable salt thereof.

9. A pharmaceutical composition which comprises a pharmaceutically acceptable carrier and an effective amount of a compound of formula I

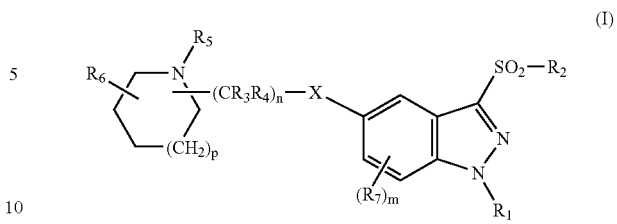

wherein
X is O, S, NR, $CH_2$, CO, $CH_2O$, $CH_2S$, $CH_2NR$, $CH_2CO$, CONR or NRCO;
n is 0 or an integer of 1, 2, 3, 4, 5, or 6;
$R_1$ is H or an optionally substituted alkyl group;
$R_1$ is H or an alkyl, cycloalkyl, aryl or heteroaryl group each optionally substituted;
$R_2$ is an optionally substituted alkyl, cycloalkyl, aryl or heteroaryl group or an optionally substituted 8- to 13-membered bicyclic or tricyclic ring system having a N atom at the bridgehead and optionally containing 1, 2 or 3 additional heteroatoms selected from N, O or S;
$R_3$ and $R_4$ are each independently H, or an optionally substituted alkyl group;
$R_5$ is H, $COR_{12}$ or an alkyl, alkenyl, alkynyl, cycloalkyl, cycloheteroalkyl, aryl or heteroaryl group each optionally substituted;
$R_6$ is H or an optionally substituted alkyl group;
p is the integer 1;
$R_7$ is H, halogen, CN, $OR_8$, $CO_2R_9$, $CONR_{10}R_{11}$, or an alkyl, alkenyl, alkynyl, cycloalkyl, cycloheteroalkyl, aryl or heteroaryl group each optionally substituted;
m is an integer of 1, 2 or 3;
$R_8$ is H, $COR_{12}$ or an alkyl, alkenyl, alkynyl, aryl or heteroaryl group each optionally substituted;
$R_9$ is H or a $C_1$-$C_6$alkyl, aryl or heteroaryl group each optionally substituted;
$R_{10}$ and $R_{11}$ are each independently H or an optionally substituted alkyl group; and
$R_{12}$ is an optionally substituted $C_1$-$C_6$alkyl, cycloalkyl, cycloheteroalkyl, aryl or heteroaryl group; or
a stereoisomer thereof or a pharmaceutically acceptable salt thereof.

10. The composition according to claim 9 having a formula I compound wherein X is O, NR, or $CH_2$.

11. The composition according to claim 10 having a formula I compound wherein n is 0 or 1.

12. The composition according to claim 11 having a formula I compound wherein X is O or NH; and $R_2$ is an optionally substituted naphthyl or imidazothiazolyl group.

13. The composition according to claim 9 having a formula I compound selected from the group consisting of:
3-(1-naphthylsulfonyl)-5-(piperidin-4-yloxy)-1H-indazole;
3-(1-naphthylsulfonyl)-5-[(1-propylpiperidin-4-yloxy]-1H-indazole;
5-[(1-butylpiperidin-4-yl)oxy]-3-(1-naphthylsulfonyl)-1H-indazole;
5-[(1-methylpiperidin-4-yl)oxy-]-3-(1-naphthylsulfonyl)-1H-indazole;
5-[(1-isopropylpiperidin-4-yloxy]-3-(1-naphthylsulfonyl)-1H-indazole;
3-(1-naphthylsulfonyl)-5-{[1-(2-phenylethyl)piperidin-4-yl]oxy}-1H-indazole;

5-[(1-ethylpiperidin-4-yl)oxy]-3-(1-naphthylsulfonyl)-1H-indazole;
3-(1-naphthylsulfonyl)-5-(piperidin-4-ylmethoxy)-1H-indazole;
3-(1-naphthylsulfonyl)-5-(piperidin-3-ylmethoxy)-1H-indazole;
3-(1-naphthylsulfonyl)-5-(piperidin-3-yloxy)-1H-indazole;
3-(1-naphthylsulfonyl)-N-piperidin-4-yl-1H-indazol-5-amine;
3-(1-naphthylsulfonyl)-N-(piperidin-4-ylmethyl)-1H-indazol-5-amine;
3-(1-naphthylsulfonyl)-N-piperidin-3-yl-1H-indazol-5-amine;
N-[3-(1-naphthylsulfonyl)-1H-indazol-5-yl]piperidine-4-carboxamide;
3-(phenylsulfonyl)-5-(piperidin-4-yloxy)-1H-indazole;
3-[(3-fluorophenyl)sulfonyl]-5-(piperidin-4-yloxy)-1H-indazole;
3-[(2-chlorophenyl)sulfonyl]-5-(piperidin-4-yloxy)-1H-indazole;
3-[(3-chlorophenyl)sulfonyl]-5-(piperidin-4-yloxy)-1H-indazole;
3-[(4-chlorophenyl)sulfonyl]-5-(piperidin-4-yloxy)-1H-indazole;
3-[(3-methylphenyl)sulfonyl]-5-(piperidin-4-yloxy)-1H-indazole;
3-[(3-methoxyphenyl)sulfonyl]-5-(piperidin-4-yloxy)-1H-indazole;
3-[(4-methoxyphenyl)sulfonyl]-5-(piperidin-4-yloxy)-1H-indazole;
5-(piperidin-4-yloxy)-3-{[3-(trifluoromethyl)phenyl]sulfonyl}-1H-indazole;
5-(piperidin-4-yloxy)-3-{[4-(trifluoromethyl)phenyl]sulfonyl}-1H-indazole;
3-[(4-isopropylphenyl)sulfonyl]-5-(piperidin-4-yloxy)-1H-indazole;
3-[(4-methyl-1-naphthyl)sulfonyl]-5-(piperidin-4-yloxy)-1H-indazole;
3-[(3-chlorophenyl)sulfonyl]-N-piperidin-4-yl-1H-indazol-5-amine;
3-[(4-chlorophenyl)sulfonyl]-N-piperidin-4-yl-1H-indazol-5-amine;
3-(2-naphthylsulfonyl)-N-piperidin-4-yl-1H-indazol-5-amine;
3-[(3-fluorophenyl)sulfonyl]-N-piperidin-4-yl-1H-indazol-5-amine;
3-[(4-fluorophenyl)sulfonyl]-N-piperidin-4-yl-1H-indazol-5-amine;
3-[(4-isopropylphenyl)sulfonyl]-N-piperidin-4-yl-1H-indazol-5-amine;
N-piperidin-4-yl-3-{[4-(trifluoromethyl)phenyl]sulfonyl}-1H-indazol-5-amine;
3-(phenylsulfonyl)-N-piperidin-4-yl-1H-indazol-5-amine;
3-[(4-methoxyphenyl)sulfonyl]-N-piperidin-4-yl-1H-indazol-5-amine; and
3-[(3-methylphenyl)sulfonyl]-N-piperidin-4-yl-1H-indazol-5-amine; or
a stereoisomer thereof; or
a pharmaceutically acceptable salt thereof.

14. A process for the preparation of a compound of formula I

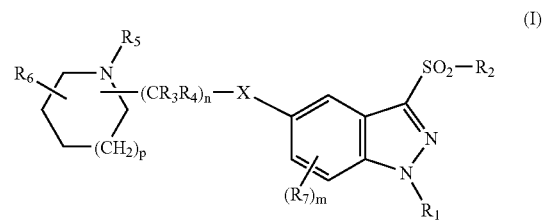

wherein
X is O, S, NR, $CH_2$, CO, $CH_2O$, $CH_2S$, $CH_2NR$, $CH_2CO$, CONR or NRCO;
n is 0 or an integer of 1, 2, 3, 4, 5, or 6;
R is H or an optionally substituted alkyl group;
$R_1$ is H or an alkyl, cycloalkyl, aryl or heteroaryl group each optionally substituted;
$R_2$ is an optionally substituted alkyl, cycloalkyl, aryl or heteroaryl group or an optionally substituted 8- to 13-membered bicyclic or tricyclic ring system having a N atom at the bridgehead and optionally containing 1, 2 or 3 additional heteroatoms selected from N, O or S;
$R_3$ and $R_4$ are each independently H, or an optionally substituted alkyl group;
$R_5$ is H, $COR_{12}$ or an alkyl, alkenyl, alkynyl, cycloalkyl, cycloheteroalkyl, aryl or heteroaryl group each optionally substituted;
$R_6$ is H or an optionally substituted alkyl group;
p is the integer 1;
$R_7$ is H, halogen, CN, $OR_8$, $CO_2R_9$, $CONR_{10}R_{11}$, or an alkyl, alkenyl, alkynyl, cycloalkyl, cycloheteroalkyl, aryl or heteroaryl group each optionally substituted;
m is an integer of 1, 2 or 3;
$R_8$ is H, $COR_{12}$ or an alkyl, alkenyl, alkynyl, aryl or heteroaryl group each optionally substituted;
$R_9$ is H or a $C_1$-$C_6$alkyl, aryl or heteroaryl group each optionally substituted;
$R_{10}$ and $R_{11}$ are each independently H or an optionally substituted alkyl group; and
$R_{12}$ is an optionally substituted $C_1$-$C_6$alkyl, cycloalkyl, cycloheteroalkyl, aryl or heteroaryl group;
which process comprises reacting a compound of formula II

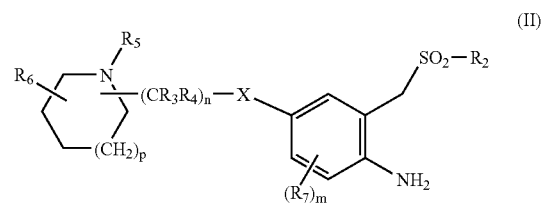

wherein X, $R_2$, $R_3$, $R_4$, $R_5$, $R_6$, $R_7$, m, n and p are as described hereinabove for formula I with $NaNO_2$ in the presence of an acid to give the compound of formula I wherein $R_1$ is H; and optionally reacting said compound with $R_1$-Hal wherein Hal is Cl, Br or I and $R_1$ is an alkyl, cycloalkyl aryl or heteroaryl group each optionally substituted.

* * * * *